(12) United States Patent
Gaucher

(10) Patent No.: US 8,940,861 B2
(45) Date of Patent: Jan. 27, 2015

(54) VARIANTS OF ANCESTRAL URICASES AND USES THEREOF

(75) Inventor: Eric A. Gaucher, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 654 days.

(21) Appl. No.: 13/083,011

(22) Filed: Apr. 8, 2011

(65) Prior Publication Data

US 2011/0268713 A1 Nov. 3, 2011

Related U.S. Application Data

(60) Provisional application No. 61/322,094, filed on Apr. 8, 2010.

(51) Int. Cl.
| | | |
|---|---|---|
| C07K 14/47 | (2006.01) | |
| A61K 38/44 | (2006.01) | |
| C12N 9/06 | (2006.01) | |
| A61K 38/00 | (2006.01) | |

(52) U.S. Cl.
CPC ............ *C12N 9/0046* (2013.01); *A61K 38/00* (2013.01); *Y10S 530/846* (2013.01)
USPC ........... 530/324; 530/350; 530/846; 424/94.4

(58) Field of Classification Search
CPC ........... C12Y 107/03003; A61K 38/44; C12N 9/0048
USPC ........................ 530/324, 350, 846; 424/94.4
See application file for complete search history.

(56) References Cited

U.S. PATENT DOCUMENTS

| | | | |
|---|---|---|---|
| 6,576,235 B1 * | 6/2003 | Williams et al. ............. | 424/94.4 |
| 6,783,965 B1 | 8/2004 | Sherman et al. | |
| 7,056,713 B1 | 6/2006 | Hershfield et al. | |
| 7,723,089 B2 | 5/2010 | Williams et al. | |
| 7,811,800 B2 | 10/2010 | Hartman et al. | |
| 2009/0169534 A1 | 7/2009 | Hartman et al. | |
| 2012/0269795 A1* | 10/2012 | Fan et al. ..................... | 424/94.4 |

OTHER PUBLICATIONS

International Search Report and Written Opinion of International Application No. PCT/US2011/031761, mailed Dec. 26, 2011 (14 pages).
Oda et al. "Loss of Urate Oxidase Activity in Hominoids and its Evolutionary Implications" *Molecular Biology and Evolution* 19(5):640-653 (2002).
NCBI Reference Sequence No. NP_001011886.1, Uricase (*Canis lupus familiaris*), created Feb. 11, 2005 (2 pages).
Sherman et al. "PEG-Uricase in the Management of Treatment-Resistant Gout and Hyperuricemia" *Advanced Drug Delivery Reviews* 60:59-68 (2008).
Swiss-Prot. No. P25689.3, URIC-PAPHA, created May 1, 1992 (4 pages).
Swiss-Prot. No. Q8MK3.3, Uricase (Urate oxidase), created May 1, 2005 (2 pages).
Wu et al. "Urate Oxidase: Primary Structure and Evolutionary Implications" *PNAS USA* 86:9412-9416 (1989).

* cited by examiner

*Primary Examiner* — Anne Marie S Wehbe
(74) *Attorney, Agent, or Firm* — Myers Bigel Sibley & Sajovec, P.A.

(57) ABSTRACT

The present invention provides uricases and methods of their production and use in reducing the amount of uric acid in a subject. The present invention further provides methods employing a uricase of this invention in the treatment and/or prevention of hyperuricemia, gout, tumor lysis syndrome and/or hypertension in a subject.

4 Claims, 3 Drawing Sheets

US 8,940,861 B2

VARIANTS OF ANCESTRAL URICASES AND USES THEREOF

RELATED APPLICATIONS

This application claims priority under 35 U.S.C. §119(e) to U.S. Provisional Application No. 61/322,094, filed Apr. 8, 2010, the disclosure of which is incorporated herein by reference in its entirety.

FIELD OF THE INVENTION

The present invention relates to ancestral forms of mammalian uricases and uses thereof.

BACKGROUND

Uric acid, a natural breakdown product of DNA, RNA and ATP, is considered to be one of the most important antioxidants in blood plasma. Most mammals rely on uricase enzymes to maintain a uric acid plasma concentration of around 1-2 mg/dl. Humans however, must rely on their kidneys to excrete most of the uric acid that is produced because the current human gene form is incapable of producing a functional uricase enzyme.

Abnormally high uric acid levels have been associated with numerous disease states, including gout and tumor lysis syndrome.

Recombinant uricases are administered for the treatment of gout and as a prophylaxis against hyperuricemia caused by tumor lysis syndrome. The currently available uricase therapeutics, which comprise nonhuman uricase enzymes, are either ineffective or elicit undesirable immune responses (sometimes leading to anaphylactic shock or even death). See U.S. Pat. Nos. 6,783,965; 7,056,713; 7,723,089 and 7,811,800 and U.S. Patent Publication No. 2009/0169534.

The present invention overcomes these problems by reconstructing and resurrecting ancestral forms of the current human uricase enzyme. Uricases of the present invention may be used therapeutically in humans to reduce uric acid levels without eliciting an undesirable immune response.

SUMMARY OF THE INVENTION

The present invention provides uricases and uricase subunits, which represent ancestral forms of mammalian uricases or variants thereof.

Uricases of the present invention can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to one or more of the respective amino acid sequences of SEQ ID NOs:1-9. Uricases of the present invention may be homomers or heteromers and may be conjugated to one or more oligomers, such as polyethylene glycol (PEG).

The present invention also provides nucleic acid molecules comprising one or more nucleotide sequences encoding one or more uricase subunits of the present invention and methods of using those nucleic acid molecules to produce a uricase of the present invention.

The present invention also provides vectors comprising one or more nucleic acid molecules of the present invention and methods of using a vectors of this invention to produce a uricase of the present invention.

The present invention also provides cells that produce one or more uricase subunits and uricases of the present invention and methods of using those cells to produce uricases of the present invention.

The present invention also provides pharmaceutical compositions comprising one or more uricases, nucleic acid molecules, vectors and/or cells of the present invention in a pharmaceutically acceptable carrier.

The present invention also provides a method of reducing the amount of uric acid in a subject, comprising administering to the subject an effective amount of a uricase of the present invention. A method is also provided of reducing the amount of uric acid in a subject, comprising administering to the subject an effective amount of a composition of this invention comprising a uricase of this invention and a pharmaceutically acceptable carrier.

The present invention also provides a method of treating and/or preventing hyperuricemia, gout, tumor lysis syndrome and/or hypertension in a subject (e.g., a subject in need thereof), comprising administering to the subject an effective amount of a uricase of this invention and/or a nucleic acid molecule comprising a nucleotide sequence encoding one or more uricase subunits of this invention. Also provided herein is a method of treating and/or preventing hyperuricemia, gout, tumor lysis syndrome and/or hypertension in a subject (e.g., a subject in need thereof), comprising administering to the subject a composition of this invention, wherein said composition comprises a uricase and/or a nucleic acid molecule of this invention and a pharmaceutically acceptable carrier.

A uricase of the present invention may possess uricolytic activity that meets or exceeds the uricolytic activity of known uricases, such as Krystexxa™ (Savient Pharmaceuticals, Inc., East Brunswick, N.J.) and Elitek® (Sanofi Aventia US, LLC, Bridgewater, N.J.).

The foregoing and other objects and aspects of the present invention are explained in detail in the drawings and description set forth below.

DETAILED DESCRIPTION OF THE INVENTION

Figure 1:
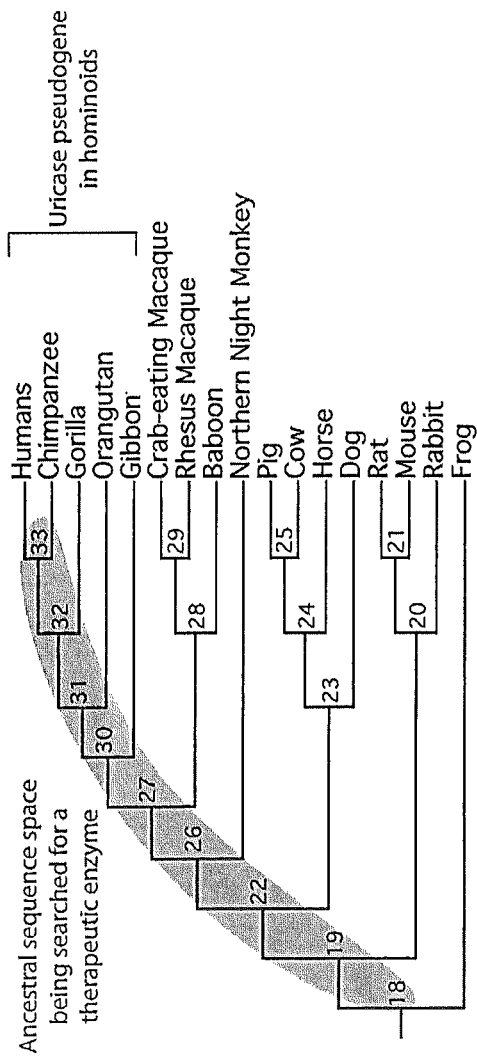
FIG. 1 is a graphical depiction of the phylogenetic tree used to reconstruct and resurrect ancestral forms of mammalian uricases. The phylogentic tree was constructed using MrBayes Version 3.1 software (available at http://mrbayes.csit.fsu.edu/download.php) using a general time reversible model with a proportion of invariable sites and a gamma-shaped rate distributions across sites. The analysis comprised two runs of one million generations, with four chains each. One hundred thousand trees were sampled and the first one hundred trees were discarded as burnin. Branch lengths are not shown.

The present invention provides uricases and uricase subunits, which represent ancestral forms of mammalian uricases or variants thereof. In addition, the present invention provides compositions and methods for metabolizing uric acid and/or reducing the amount of uric acid (e.g., a uric acid level) in a subject.

Uricases of the present invention may possess uricolytic activity that meets or exceeds the uricolytic activity of known uricases. For example, a uricase of the present invention may possess uricolytic activity that is at least about 5%, 10%, 15%, 20%, 25%, 30%, 35%, 40%, 45%, 50%, 55%, 60%, 65%, 70%, 75%, 80%, 85%, 90%, 95% 100%, 150%, 200%, 300%, 400%, 500% or more higher than the uricolytic activity of one or more known uricases (e.g., a control uricase).

Uricases of the present invention may possess thermodynamic and/or kinetic stability that meets or exceeds that of known uricases. For example, a uricase of the present invention may possess thermodynamic and/or kinetic stability that is at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more higher than that of one or more known uricases (e.g., a control uricase).

A uricase of the present invention may be used to reduce the amount of uric acid in a subject and/or to prevent an increase in the amount of uric acid in a subject. In some embodiments, a uricase of the present invention can be used to reduce the amount of uric acid in a subject and/or to prevent an increase in the amount of uric acid in a subject while minimizing an undesirable immune response in the subject. In some embodiments, a uricase of the present invention can be administered in a therapeutically effective dose without eliciting any appreciable immunoreactivity to the uricase.

DEFINITIONS

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" cell can mean one cell or a plurality of cells.

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the term "antigenicity" refers to the reaction of an antibody with an antigen, such as uricase.

As used herein, the term "consists essentially of" (and grammatical variants thereof), as applied to the uricases, nucleic acid molecules, vectors, cells, compositions and methods of the present invention, means that the additional components and/or method steps may be added so long as the additional components and/or steps do not materially alter the basic and novel characteristics of the present invention. For example, as it is applied to a polynucleotide or polypeptide sequence of this invention, "consists essentially of" means that the polynucleotide or polypeptide sequence may consist of both the recited sequence (e.g., SEQ ID NO:2) and a total of ten or fewer (i.e., 1, 2, 3, 4, 5, 6, 7, 8, 9 or 10) additional nucleotides or amino acids such that the function of the polynucleotide or polypeptide sequence is not materially altered. The additional nucleotides or amino acids may be added to either end (or to both ends) of the recited sequence (i.e., the total number of additional nucleotides or amino acids includes the total number at both ends added together). The term "materially altered," as applied to polynucleotides of the invention, refers to an increase or decrease in ability to express the polynucleotide of at least about 10%, 20%, 30%, 40%, 50% or more as compared to the expression level of a polynucleotide consisting of the recited sequence. The term "materially altered," as applied to polypeptides of the invention, refers to an increase or decrease in activity (e.g., uricolytic activity) of at least about 10%, 20%, 30%, 40%, 50% or more as compared to the activity of a polypeptide consisting of the recited sequence.

As used herein, the term "gout" refers to a condition characterized by an elevated uric acid level and the formation of uric acid crystals in one or more joints. Subjects with gout may experience a variety of symptoms, including, but not limited to, acute and/or chronic pain in one or more joints, swelling and fever.

As used herein, the term "immunogenicity" refers to the induction of an immune response to an antigen following administration of the antigen (i.e., an immunogen such as uricase.

As used herein, the term "immunoreactivity" refers to both antigenicity and immunogenicity. In general, immunoreactivity to a given antigen is assessed by monitoring/measuring 1) the reaction of preexisting antibodies with the antigen, 2) the production of antibodies directed against the antigen and 3) the rate at which the antigen is cleared following repeated administrations.

Non-limiting examples of an immune response as described herein include an antibody response (e.g., protective antibody response; neutralizing antibody response; antibody dependent cellular cytotoxicity), a cellular response (e.g., cytotoxic T cell response; T helper response; interleukin-2 (IL-2) production; regulatory T cell (Treg) response; T helper 1 (Th1) response; T helper 2 (Th2) response; T helper 17 (Th17) response), an innate response (e.g., dendritic cell, natural killer cell, macrophage, polymorphonuclear cell (neutrophil)), and any combination thereof. The uricases of the present invention are designed to minimize or reduce any such immune response that may be deleterious or undesirable to elicit in a subject of this invention.

As used herein, the term "isolated," as applied to nucleic acid molecules, proteins or protein fragments of the present invention, means that the nucleic acid or protein or protein fragment is sufficiently free of contaminants and/or cell components with which nucleic acids or proteins normally occur. "Isolated" does not mean that the preparation is technically pure (homogeneous), but rather that it is sufficiently pure to provide the nucleic acid or protein or protein fragment in a form in which it can be used therapeutically.

An "isolated cell" as used herein is a cell or population of cells that have been removed from the environment in which the cell occurs naturally and/or altered or modified from the state in which the cell occurs in its natural environment. An isolated cell of this invention can be a cell, for example, in a cell culture. An isolated cell of this invention can also be a cell that can be in an animal and/or introduced into an animal and wherein the cell has been altered or modified, e.g., by the introduction into the cell of a protein, nucleic acid molecule and/or vector of this invention.

The terms "mutant," "mutation," and other grammatical variants encompass, at the amino acid sequence level of a uricase subunit of this invention, any substitution with any naturally occurring amino acid residue (Table 1), any substitution with any non-naturally occurring amino acid residue (e.g., one or more of the non-naturally occurring amino acids listed in Table 2), any deletion, any insertion, and any combination thereof in a wild type amino acid sequence of a uricase subunit. These terms are also intended to encompass the incorporation of additional glycosylation sites into the uricase subunit of this invention, as well as modifications in the amino acid sequence of the uricase subunit that result in an alteration of the framework of the subunit and/or a tetramer/octamer comprising the subunit.

These mutations can be introduced at the nucleic acid level by altering or modifying the nucleotide sequence encoding the uricase subunit (e.g., to introduce into the nucleotide sequence a deletion, substitution, insertion, stop codon, missense mutation, nonsense mutation, etc.) according to well known methods to produce the desired mutation at the amino acid sequence level. The result of these mutations is the phenotype of enhanced urolytic activity and, optionally, enhanced thermodynamic and/or kinetic stability, as defined herein. The production and testing of such mutants to identify those with the phenotype of this invention can be carried out according to methods well known in the art and as described herein.

TABLE 1

| NATURALLY OCCURRING AMINO ACID RESIDUE | ABBREVIATION | |
|---|---|---|
| | THREE-LETTER CODE | ONE-LETTER CODE |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

| NON-NATURALLY OCCURRING AMINO ACID RESIDUE | ABBREVIATION |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |

TABLE 2-continued

| NON-NATURALLY OCCURRING AMINO ACID RESIDUE | ABBREVIATION |
|---|---|
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

As used herein, the term "pharmaceutically acceptable" means that a compound or composition is suitable for administration to a subject to achieve the desired effect or treatment without unduly deleterious side effects in light of the severity of the disorder or disease and the necessity of the treatment. For example, a "pharmaceutically acceptable carrier" may be a material that is relatively non-toxic and innocuous to a subject at concentrations consistent with effective activity of the active ingredient so that any side effects ascribable to the carrier do not vitiate the beneficial effects of the active ingredient (e.g., a non-toxic material that may be administered to a subject without causing any undesirable biological effects and without interfering with the uricolytic activity of a uricase of the present invention).

The terms "prevent," "prevention," "preventing" and "attenuating" (and grammatical variations of each of those terms) refer to prevention and/or delay of the onset of a disease, disorder and/or a clinical signs and/or symptom(s) in a subject and/or a reduction or attenuation in the severity of the onset of the disease, disorder and/or clinical symptom(s) relative to what would occur in the absence of the methods of the invention. The prevention can be complete, e.g., the total absence of the disease, disorder and/or clinical signs and/or symptom(s). The prevention can also be partial, such that the occurrence of the disease, disorder and/or clinical signs and/or symptom(s) in the subject and/or the severity of onset is less than what would occur in the absence of the present invention (i.e., attenuated).

A "prevention effective" amount as used herein is an amount that is sufficient to prevent and/or delay the onset of a disease, disorder and/or clinical signs and/or symptoms in a subject and/or to reduce and/or delay the severity of the onset of a disease, disorder and/or clinical signs and/or symptoms in a subject relative to what would occur in the absence of the methods of the invention. Those skilled in the art will appreciate that the level of prevention need not be complete, as long as some benefit is provided to the subject.

As used herein, the term "subject" (and grammatical variants thereof) refers to mammals, avians, reptiles, amphibians and fish. Mammalian subjects may include, but are not limited to, humans, non-human primates (e.g., gorillas, chimpanzees, gibbons, baboons, orangutans, macaques, monkeys, etc.), pigs, cows, horses, sheep, goats, dogs, cats, rats, mice, hamsters, guinea pigs and rabbits. In particular embodiments, the subject is a human. Avian subjects may include, but are not limited to, chickens, turkeys, ducks, geese, quail and pheasant, and birds kept as pets (e.g., parakeets, parrots, macaws, cockatoos, and the like). In some embodiments, the subject is from an endangered species. In some embodiments, the subject is a laboratory animal. Human subjects may include neonates, infants, juveniles, adults, and geriatric subjects.

As used herein, the terms "effective amount" or "therapeutically effective amount" or "treatment effective amount" refer to an amount that produces a biological effect in a subject, which can be an improvement and/or benefit to a subject. Alternatively stated, an "effective amount" or "therapeutically effective amount" or "treatment effective amount" is an amount that alleviates, reduces the severity of delays the onset of and/or inhibits the progress of at least one clinical symptom in the subject. Those skilled in the art will appreciate that the improvement and/or benefit need not be complete or curative, so long as some benefit is provided to the subject.

As used herein, the terms "treat," "treatment," and "treating" refer to reversing, alleviating, reducing the severity of, delaying the onset of, and/or inhibiting the progress of a disease or disorder as described herein, or at least one symptom of a disease or disorder as described herein (e.g., alleviating joint pain or reducing the amount of uric acid present in one or more bodily fluids, such as plasma or whole blood). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence.

As used herein, the term "tumor lysis syndrome" refers to complications resulting from massive spontaneous or chemotheraphy-induced cytolysis. The destruction of tumor cells and the release of their intracellular contents into the extracellular space leads to elevated levels of uric acid; which deposits in the tubules of the kidneys and lead to acute renal failure.

As used herein, the terms "uricase" and "uric acid oxidase" are used interchangeably to refer to enzymes that catalyze the oxidation of uric acid. Unless otherwise indicated, "uricase" refers to a tetrameric or octameric uricase enzyme, and "uricase subunit" refers to a monomeric uricase protein molecule that may assemble with other monomeric uricase protein molecules to form a tetrameric or octameric unease enzyme.

As used herein, the term "uricolytic activity" is expressed in International Units (IU), wherein an IU of uricase is defined as the amount of enzyme that consumes one micromole of uric acid per minute.

Uricases

Uricases of the present invention represent ancestral forms of mammalian uricases or variants thereof. In some embodiments, the uricase represents an ancestral form of a human uricase or a variant (e.g., mutated form) thereof.

Uricases of the present invention can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to one or more of the respective amino acid sequences of SEQ ID NOs:1-9. For example, uricases of the present invention can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to one or more of the respective amino acid sequences of SEQ ID NO:1, SEQ ID NO:2, SEQ ID NO:3, SEQ ID NO:4, SEQ IDNO:5, SEQ ID NO:6, SEQ IDNO:7, SEQ ID NO:8 and SEQ ID NO:9.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:1. In some such embodiments, the uricase can comprise, consist essentially of or consist of one or more uricase subunits having an amino acid sequence that is at least 90% identical to the amino acid sequence of SEQ ID NO:1. In some embodiments, the unease can comprise, consist essentially of or consist of one or more uricase subunits having an amino acid sequence that is at least 95% identical to the amino acid sequence of SEQ ID NO:1. In some embodiments, the amino acid at one or more of positions 96, 103, 146, 147, 192, 208, 220, 230 and 303 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:1. In some embodiments, the uricase can comprise, consist essentially of or consist of one or more uricase subunits having an amino acid sequence that is 100% identical to the amino acid sequence of SEQ ID NO:1.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:2. In some embodiments, the uricase can comprise, consist essentially of or consist of one or more uricase subunits having an amino acid sequence that is at least 96% identical to the amino acid sequence of SEQ ID NO:2. In some embodiments, the amino acid at one or more of positions 96, 103, 146, 147, 192, 208, 220, 230 and 303 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:2. In some embodiments, the uricase can comprise, consist essentially of or consist of one or more uricase subunits having an amino acid sequence that is 100% identical to the amino acid sequence of SEQ ID NO:2.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:3. In some embodiments, the can comprise, consist essentially of or consist of one or more uricase subunits having an amino acid sequence that is at least 95% identical to the amino acid sequence of SEQ ID NO:3. In some such embodiments, the uricase can comprise, consist essentially of or consist of one or more uricase subunits having an amino acid sequence that is at least 98% identical to the amino acid sequence of SEQ ID NO:3. In some embodiments, the amino acid at one or more of positions 96, 103, 146, 147, 192, 208, 220, 230 and 303 of the amino acid sequence of SEQ ID NO:3 is lysine. In some embodiments, the uricase can comprise, consist essentially of or consist of one or more uricase subunits having an amino acid sequence that is 100% identical to the amino acid sequence of SEQ ID NO:3.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:4. In some embodiments, the uricase can comprise, consist essentially of or consist of one or more uricase subunits having an amino acid sequence that is at least 94% identical to the amino acid sequence of SEQ ID NO:4. In some such embodiments, the can comprise, consist essentially of or consist of one or more uricase subunits having an amino acid sequence that is at least 99% identical to the amino acid sequence of SEQ ID NO:4. In some embodiments, the amino acid at one or more of positions 96, 103, 146, 147, 192, 208, 220, 230 and 303 of the amino acid sequence of SEQ ID NO:4 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:4. In some embodiments, the uricase can comprise, consist essentially of or consist of one or more uricase subunits having an amino acid sequence that is 100% identical to the amino acid sequence of SEQ ID NO:4.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:5. In some embodiments, the uricase can comprise, consist essentially of or consist of one or more uricase subunits having an amino acid sequence that is at least 94% identical to the amino acid sequence of SEQ ID NO:5. In some such embodiments, the can comprise, consist essentially of or consist of one or more uricase subunits having an amino acid sequence that is at least 99% identical to the amino acid sequence of SEQ ID NO:5. In some embodiments, the amino acid at one or more of positions 96, 103, 146, 147, 192, 208, 220, 230 and 303 of the amino acid sequence of SEQ ID NO:5 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:5. In some embodiments, the can comprise, consist essentially of or consist of one or more uricase subunits having an amino acid sequence that is 100% identical to the amino acid sequence of SEQ ID NO:5.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:6. In some embodiments, the uricase can comprise, consist essentially of or consist of one or more uricase subunits having an amino acid sequence that is at least 93% identical to the amino acid sequence of SEQ ID NO:6. In some such embodiments, the can comprise, consist essentially of or consist of one or more uricase subunits having an amino acid sequence that is at least 98% identical to the amino acid sequence of SEQ ID NO:6. In some embodiments, the amino acid at one or more of positions 96, 103, 146, 147, 192, 208, 220, 230 and 303 of the amino acid sequence of SEQ ID NO:6 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:6. In some embodiments, the can comprise, consist essentially of or consist of one or more uricase subunits having an amino acid sequence that is 100% identical to the amino acid sequence of SEQ ID NO:6.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:7. In some embodiments, the uricase can comprise, consist essentially of or consist of one or more uricase subunits having an amino acid sequence that is at least 91% identical to the amino acid sequence of SEQ ID NO:7. In some such embodiments, the can comprise, consist essentially of or consist of one or more uricase subunits having an amino acid sequence that is at least 98% identical to the amino acid sequence of SEQ ID NO:7. In some embodiments, the amino acid at one or more of positions 96, 103, 146, 147, 192, 208, 220, 230 and 303 of the amino acid sequence of SEQ ID NO:7 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:7. In some embodiments, the uricase can comprise, consist essentially of or consist of one or more uricase subunits having an amino acid sequence that is 100% identical to the amino acid sequence of SEQ ID NO:7.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:8. In some embodiments, the uricase can comprise, consist essentially of or consist of one or more uricase subunits having an amino acid sequence that is at least 90% identical to the amino acid sequence of SEQ ID NO:8. In some such embodiments, the uricase can comprise, consist essentially of or consist of one or more uricase subunits having an amino acid sequence that is at least 95% identical to the amino acid sequence of SEQ ID NO:8. In some embodiments, the uricase can comprise, consist essentially of or consist of one or more uricase subunits having an amino acid sequence that is 100% identical to the amino acid sequence of SEQ ID NO:8. That is, in some embodiments, the uricase can comprise, consist essentially of or consist of one or more uricase subunits having the amino acid sequence of Formula I (SEQ ID NO:8):

Formula I (SEQ ID NO: 8)

MAHYHX$_1$X$_2$X$_3$X$_4$KNX$_5$EVEFVRTGYGKX$_6$X$_7$VKVLHIQRDGKX$_8$HX$_9$

IKEVATSVQLTLX$_{10}$SKKDYLHGDNSDIIPTDTIKNTVHVLAKFKX$_{11}$

IKX$_{12}$IEAFX$_{13}$X$_{14}$NIX$_{15}$X$_{16}$HFLSSFX$_{17}$HVIRAQVYX$_{18}$EEX$_{19}$

PWKX$_{20}$X$_{21}$X$_{22}$KNGVX$_{23}$HVHAFIHTPTGTHFCEVEQX$_{24}$X$_{25}$X$_{26}$

GPX$_{27}$VIHSGIKDLKVLKTTQSGFEGFIX$_{28}$DX$_{29}$X$_{30}$TTLPEVKDRCF

ATX$_{31}$VYCKWRYX$_{32}$QX$_{33}$RX$_{34}$VDFX$_{35}$AX$_{36}$WDTX$_{37}$X$_{38}$DX$_{39}$VX$_{40}$X$_{41}$

KX$_{42}$AGPYDKX$_{43}$X$_{44}$YX$_{45}$X$_{46}$SVQKTLX$_{47}$DIQVLSLSRVPX$_{48}$IED

MEISLPNIHX$_{49}$FNIDMSKX$_{50}$GLINKEEVLLPLX$_{51}$NPYGKITGTVKR

KLSSX$_{52}$L, wherein $X_1$ is N or G; $X_2$ is D, N or H; $X_3$ is Y or L; $X_4$ is K or T; $X_5$ is D or A; $X_6$ is D or E; $X_7$ is M or V; $X_8$ is Y or H; $X_9$ is S or I; $X_{10}$ is S or N; $X_{11}$ is G or E; $X_{12}$ is S or T; $X_{13}$ is A or G; $X_{14}$ is M or V; $X_{15}$ is C or G; $X_{16}$ is E or K; $X_{17}$ is N or K; $X_{18}$ is V or M; $X_{19}$ is V or I; $X_{20}$ is R or H; $X_{21}$ is F or L; $X_{22}$ is E or G; $X_{23}$ is K or N; $X_{24}$ is M, L or K; $X_{25}$ is R or K; $X_{26}$ is S or G; $X_{27}$ is P or Q; $X_{28}$ is K or R; $X_{29}$ is Q, R or E; $X_{30}$ is F or Y; $X_{31}$ is Q or K; $X_{32}$ is H or D; $X_{33}$ is G, C or S; $X_{34}$ is D or A; $X_{35}$ is E or K; $X_{36}$ is T or I; $X_{37}$ is V or I; $X_{38}$ is R or L; $X_{39}$ is I or L; $X_{40}$ is L or M; $X_{41}$ is E or K; $X_{42}$ is F or S; $X_{43}$ is G or D; $X_{44}$ is E or K; $X_{45}$ is S or L; $X_{46}$ is P or T; $X_{47}$ is Y or C; $X_{48}$ is E or A; $X_{49}$ is Y or L; $X_{50}$ is M or G; $X_{51}$ is D, S or C and $X_{52}$ is R or K. In some embodiments, the amino acid at one or more of positions 96, 103, 146, 147, 192, 208, 220, 230 and 303 of the amino acid sequence of SEQ ID NO:8 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:8.

In some embodiments, the uricase can comprise, consist essentially of or consist of one or more uricase subunits having an amino acid sequence that is at least about 50%, 55%, 60%, 65% 70%, 75%, 80%, 85%, 90%, 95%, 96%, 97%, 98%, 99% or 100% identical to the amino acid sequence of SEQ ID NO:9. In some embodiments, the uricase can comprise, consist essentially of or consist of one or more uricase subunits having an amino acid sequence that is at least 98% identical to the amino acid sequence of SEQ ID NO:9. In some such embodiments, the can comprise, consist essentially of or consist of one or more uricase subunits having an amino acid sequence that is at least 99% identical to the amino acid sequence of SEQ ID NO:9. In some embodiments, the amino acid at one or more of positions 96, 103, 146, 147, 192, 208, 220, 230 and 303 of the amino acid sequence of SEQ ID NO:9 is lysine. In some embodiments, the stability of the uricase may be enhanced by the presence of an R at amino acid position 175, an E at amino acid position 177, a Y at amino acid position 178, an L at amino acid position 265, a G at amino acid position 273 and/or an S or a C at amino acid position 286 of the amino acid sequence of SEQ ID NO:9. In some embodiments, the uricase can comprise, consist essentially of or consist of one or more ukase subunits having an amino acid sequence that is 100% identical to the amino acid sequence of SEQ ID NO:9.

Uricases of the present invention may be homotetramers or homooctamers. In some embodiments, the uricase can comprise, consist essentially of or consist of four/eight identical uricase subunits having an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. For example, the uricase can comprise, consist essentially of or consist of four/eight identical uricase subunits having an amino acid sequence that is at least about 50%, 55%, 60%, 65% 70%, 75%, 80%, 85%, 90%, 95%, 96%, 97%, 98%, 99% or 100% identical to amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9 (e.g., four/eight identical uricase subunits having an amino acid sequence that is at least 96% identical to the amino acid sequence of SEQ ID NO:2). In some embodiments, the uricase can comprise, consist essentially of or consist of four/eight identical uricase subunits having an amino acid sequence that is 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. For example, the uricase can comprise, consist essentially of or consist of four/eight identical uricase subunits having an amino acid sequence that is 100% identical to the amino acid sequence of SEQ ID NO:1, SEQ ID NO:2, SEQ ID NO:3, SEQ ID NO:4, SEQ ID NO:5, SEQ ID NO:6,SEQ ID NO:7, SEQ ID NO: 8 or SEQ ID NO:9 (e.g., each of the four/eight uricase subunits consists of the amino acid sequence of SEQ ID NO:2).

Uricases of the present invention may be heterotetramers or heterooctamers, comprising at least two (e.g., 2, 3, 4, 5, 6, 7 or 8) distinct uricase subunits. For example, the uricase can comprise, consist essentially of or consist of at least two previously known uricase subunits (e.g., at least one pig uricase subunit (SEQ ID NO:10) and at least one baboon uricase subunit (SEQ ID NO:11)), at least one uricase subunit of the present invention and at least one previously known uricase subunit (e.g., at least one uricase subunit of the present invention and at least one pig uricase subunit (SEQ ID NO:10)) or at least two distinct uricase subunits of the present invention. The heterotetramers/heterooctamers can be made up of any combination of uricase subunits and in any ratio. For example, a uricase of this invention can have one subunit comprising the amino acid sequence of SEQ ID NO:2, one subunit comprising the amino acid sequence of SEQ ID NO:3 and two subunits comprising the amino acid sequence of a wild type (nonmodified) uricase subunit.

In some embodiments, the uricase can comprise, consist essentially of or consist of a heterotetramer/heterooctamer wherein at least one of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NOs:1-9. For example, the uricase can comprise, consist essentially of or consist of a heterotetramer/heterooctamer wherein at least one of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., at least one of the uricase subunits has an amino acid sequence that is at least 96% identical to the amino acid sequence of SEQ ID NO:2).

In some embodiments, the uricase can comprise, consist essentially of or consist of a heterotetramer/heterooctamer wherein at least two of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NOs:1-9. For example, the uricase can comprise, consist essentially of or consist of a heterotetramer/heterooctamer wherein at least two of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., at least one of the uricase subunits has an amino acid sequence that is at least 96% identical to the amino acid sequence of SEQ ID NO:2 and at least one other of the uricase subunits has an amino acid sequence that is at least 95% identical to the amino acid sequence of SEQ ID NO:3).

In some embodiments, the uricase can comprise, consist essentially of or consist of a heterotetramer/heterooctamer wherein at least three of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NOs:1-9. For example, the uricase can comprise, consist essentially of or consist of a heterotetramer/heterooctamer wherein at least three of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., at least two of the uricase subunits has an amino acid sequence that is at least 96% identical to the amino acid sequence of SEQ ID NO:2 and at least one other of the uricase subunits has an amino acid sequence that is at least 95% identical to the amino acid sequence of SEQ ID NO:3).

In some embodiments, the uricase can comprise, consist essentially of or consist of a heterotetramer/heterooctamer wherein at least four of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NOs:1-9. For example, the uricase can comprise, consist essentially of or consist of a heterotetramer/heterooctamer wherein at least four of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., three of the subunits have an amino acid sequence that is at least 96% identical to the amino acid sequence of SEQ ID NO:2 and one of the subunits has an amino acid sequence that is at least 95% identical to the amino acid sequence of SEQ ID NO:3).

In some embodiments, the uricase can comprise, consist essentially of or consist of a heterooctamer wherein at least five of the uricase subunits has an amino acid sequence that is at least about 50%, 55%, 60%, 65% 70%, 75%, 80%, 85%, 90%, 95%, 96%, 97%, 98%, 99%, or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. For example, the uricase can comprise, consist essentially of or consist of a heterooctamer wherein at least five of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., at least three of the uricase subunits has an amino acid sequence that is at least 96% identical to the amino acid sequence of SEQ ID NO:2 and at least two other of the uricase subunits has an amino acid sequence that is at least 95% identical to the amino acid sequence of SEQ ID NO:3).

In some embodiments, the uricase can comprise, consist essentially of or consist of a heterooctamer wherein at least six of the uricase subunits has an amino acid sequence that is at least about 50%, 55%, 60%, 65% 70%, 75%, 80%, 85%, 90%, 95%, 96%, 97%, 98%, 99%, or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. For example, the uricase can comprise, consist essentially of or consist of a heterooctamer wherein at least six of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., at least three of the uricase subunits has an amino acid sequence that is at least 96% identical to the amino acid sequence of SEQ ID NO:2 and at least three other of the uricase subunits has an amino acid sequence that is at least 95% identical to the amino acid sequence of SEQ ID NO:3).

In some embodiments, the uricase can comprise, consist essentially of or consist of a heterooctamer wherein at least seven of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NOs:1-9. For example, the uricase can comprise, consist essentially of or consist of a heterooctamer wherein at least seven of the uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., at least three of the uricase subunits has an amino acid sequence that is at least 96% identical to the amino acid sequence of SEQ ID NO:2, at least two other of the uricase subunits has an amino acid sequence that is at least 95% identical to the amino acid sequence of SEQ ID NO:3 and at least two other of the uricase subunits has an amino acid sequence that is at least 94% identical to the amino acid sequence of SEQ ID NO:4).

In some embodiments, the uricase can comprise, consist essentially of or consist of a heterooctamer wherein each of the eight uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. For example, the uricase can comprise, consist essentially of or consist of a heterooctamer wherein each of the eight uricase subunits has an amino acid sequence that is at least about 50%, 55%, 60%, 65% 70%, 75%, 80%, 85%, 90%, 95%, 96%, 97%, 98%, 99% or 100% identical to one of the respective amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO: 8 and SEQ ID NO:9 (e.g., three of the uricase subunits has an amino acid sequence that is at least 96% identical to the amino acid sequence of SEQ ID NO:2, two other of the uricase subunits has an amino acid sequence that is at least 95% identical to the amino acid sequence of SEQ ID NO:3, two other of the uricase subunits has an amino acid sequence that is at least 94% identical to the amino acid sequence of SEQ ID NO:4 and one other of the uricase subunits has an amino acid sequence that is at least 94% identical to the amino acid sequence of SEQ ID NO:5).

In some embodiments, the uricase can comprise, consist essentially of or consist of one or more uricase subunits selected from the group consisting of:
 a) a uricase subunit having an amino acid sequence that is at least 90% identical to the amino acid sequence of SEQ ID NO:1;
 b) a unease subunit having an amino acid sequence that is at least 96% identical to the amino acid sequence of SEQ ID NO:2;
 c) a unease subunit having an amino acid sequence that is at least 95% identical to the amino acid sequence of SEQ ID NO:3;
 d) a unease subunit having an amino acid sequence that is at least 94% identical to the amino acid sequence of SEQ ID NO:4;
 e) a unease subunit having an amino acid sequence that is at least 94% identical to the amino acid sequence of SEQ ID NO:5;
 f) a unease subunit having an amino acid sequence that is at least 93% identical to the amino acid sequence of SEQ ID NO:6;
 g) a unease subunit having an amino acid sequence that is at least 91% identical to the amino acid sequence of SEQ ID NO:7;
 h) a unease subunit havng an amino acid sequence that is at least 90% identical to the amino acid sequence of SEQ ID NO:8;
 i) a unease subunit having an amino acid sequence that is at least 98% identical to the amino acid sequence of SEQ ID NO:9; and
 j) any combination of the subunits a. through i. above.

In some embodiments, the unease is a tetramer comprising, consisting essentially of or consisting of one, two, three or four distinct subunits selected from the group consisting of:
 a) a unease subunit having an amino acid sequence that is at least 90% identical to the amino acid sequence of SEQ ID NO:1;
 b) a unease subunit having an amino acid sequence that is at least 96% identical to the amino acid sequence of SEQ ID NO:2;
 c) a unease subunit having an amino acid sequence that is at least 95% identical to the amino acid sequence of SEQ ID NO:3;
 d) a unease subunit having an amino acid sequence that is at least 94% identical to the amino acid sequence of SEQ ID NO:4;
 e) a unease subunit having an amino acid sequence that is at least 94% identical to the amino acid sequence of SEQ ID NO:5;
 f) a unease subunit having an amino acid sequence that is at least 93% identical to the amino acid sequence of SEQ ID NO:6;
 g) a unease subunit having an amino acid sequence that is at least 91% identical to the amino acid sequence of SEQ ID NO:7;
 h) a uricase subunit havng an amino acid sequence that is at least 90% identical to the amino acid sequence of SEQ ID NO:8; and
 i) a uricase subunit having an amino acid sequence that is at least 98% identical to the amino acid sequence of SEQ ID NO:9.

In some embodiments, the uricase is an octamer comprising, consisting essentially of or consisting of one, two, three, four, five, six, seven or eight distinct subunits selected from the group consisting of:
 a) a uricase subunit having an amino acid sequence that is at least 90% identical to the amino acid sequence of SEQ ID NO:1;
 b) a uricase subunit having an amino acid sequence that is at least 96% identical to the amino acid sequence of SEQ ID NO:2;
 c) a uricase subunit having an amino acid sequence that is at least 95% identical to the amino acid sequence of SEQ ID NO:3;
 d) a uricase subunit having an amino acid sequence that is at least 94% identical to the amino acid sequence of SEQ ID NO:4;
 e) a uricase subunit having an amino acid sequence that is at least 94% identical to the amino acid sequence of SEQ ID NO:5;
 f) a uricase subunit having an amino acid sequence that is at least 93% identical to the amino acid sequence of SEQ ID NO:6;
 g) a uricase subunit having an amino acid sequence that is at least 91% identical to the amino acid sequence of SEQ ID NO:7;
 h) a uricase subunit having an amino acid sequence that is at least 90% identical to the amino acid sequence of SEQ ID NO:8; and
 i) a uricase subunit having an amino acid sequence that is at least 98% identical to the amino acid sequence of SEQ ID NO:9.

Conjugated Uricases

Uricases of the present invention may be conjugated to one or more oligomers. That is, one or more oligomers may be conjugated to the uricase subunits that make up a uricase of the present invention. In some embodiments, each of the uricase subunits that make up the uricase is conjugated to at least one oligomer.

Any suitable oligomer can be conjugated to uricases of the present invention, including, but limited to, poly-dispersed oligomers (such as those described in U.S. Pat. Nos. 4,179,337; 5,567,422; 5,359,030; 5,438,040; 5,681,811 and 6,309,633) and non-poly-dispersed oligomers (such as those described in U.S. patent application Ser. Nos. 09/873,731; 09/873,797 and 09/873,899).

In some embodiments, the oligomer comprises, consists essentially of or consists of a hydrophilic moiety, such as a polyalkylene glycol (including, but not limited to, polypropylene glycol, polybutylene glycol and PEG moieties) or a polyoxyethylenated polyol.

In some embodiments, the oligomer comprises, consists essentially of or consists of a lipophilic moiety, such as a saturated, linear alkyl moiety (including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl moieties) a saturated, branched alkyl moiety (including, but not limited to, isopropyl, sec-butyl, tert-butyl, 2-methylbutyl, tert-pentyl, 2-methyl-pentyl, 3-methylpentyl, 2-ethylhexyl and 2-propylpentyl moieties), an unsaturated alkyl moieties derived from the aforementioned saturated alkyl moieties (including, but not limited to, vinyl, allyl, 1-butenyl, 2-butenyl, ethynyl, 1-propynyl and 2-propynyl moieties), a natural or synthetic unsaturated fatty acid moiety (including, but not limited to, lauroleate, myristoleate, palmitoleate, oleate, elaidate, erucate, linoleate, linolenate, arachidonate, eicosapentaentoate and docosahexaenoate moieties) or a natural or synthetic saturated fatty acid moiety (including, but not limited to, acetate, caproate, caprylate, caprate, laurate, arachidate, behenate, lignocerate and cerotate moieties).

The oligomer can comprise one or more other moieties, including, but not limited to, additional hydrophilic moieties, lipophilic moieties, bonding moieties (including, but not limited to, ester, thio-ester, ether, carbamate, thio-carbamate, carbonate, thio-carbonate, amide and urea moieties and covalent bonds), spacer moieties (including, but not limited to, sugar, cholesterol and glycerine moieties), linker moieties (including, but not limited to, alkyl and fatty acid moieties as described above), and terminating moieties (including, but not limited to, alkyl, alkoxy, sugar, cholesterol, alcohol and fatty acid moieties). The various moieties in the oligomer can be covalently coupled to one another by either hydrolyzable or non-hydrolyzable bonds.

In accordance with some embodiments of the present invention, the uricase-oligomer conjugate comprises the structure of Formula II:

URICASE-BL$_w$-S$_x$-R-S$_y$-R'-S$_z$-T (Formula II)

wherein URICASE represents a uricase of the present invention, B represents a bonding moiety, L represents a linker moiety, S represents a spacer moiety, R represents a lipophilic moiety or a hydrophilic moiety, R' represents a lipophilic moiety or a hydrophilic moiety and T represents a terminating moiety, wherein R and R' cannot simultaneously represent a lipophilic moiety, wherein R and R' cannot simultaneously represent a hydrophilic moiety, and wherein w, x, y and z are individually 0 or 1.

In some embodiments, a plurality of oligomers may be conjugated to a unease of the present invention. In such embodiments, the plurality of oligomers may comprise one or more oligomer types. That is, each of the oligomers, in the plurality can be the same or the plurality may comprise at least two distinct oligomers (e.g., a first oligomer having a lipophilic moiety but no hydrophilic moiety and a second oligomer having a hydrophilic moiety but no lipophilic moiety).

In some embodiments, the conjugation of one or more oligomers to a unease of the present invention reduces the antigenicity of the unease and/or prolongs the circulating half-life of the unease. For example, conjugating one or more PEG moieties to a unease of the present invention may reduce the antigenicty of the unease by at least about 5%, 10, 20%, 30, 40%, 50%, 60%, 70%, 80%, 90% or more as compared to an unconjugated version of the same unease. Likewise, conjugating one or more PEG moieties to a unease of the present invention may prolong the circulating half-life of the unease by at least about 5%, 10, 20%, 30, 40%, 50%, 60%, 70%, 80%, 90%, 100%, 150%, 200% or more as compared to an unconjugated version of the same unease.

Nucleic Acid Molecules Encoding Uricases of the Present Invention

The present invention further provides an isolated nucleic acid molecule comprising a nucleotide sequence encoding one or more unease subunits or fragment thereof of this invention. In some embodiments, the isolated nucleic acid molecule comprises, consists essentially or of consists of a nucleic acid sequence that encodes one or more unease subunits selected from the group consisting of:
   a) a uricase subunit having an amino acid sequence that is at least 90% identical to the amino acid sequence of SEQ ID NO:1;
   b) a uricase subunit having an amino acid sequence that is at least 96% identical to the amino acid sequence of SEQ ID NO:2;
   c) a uricase subunit having an amino acid sequence that is at least 95% identical to the amino acid sequence of SEQ ID NO:3;
   d) a uricase subunit having an amino acid sequence that is at least 94% identical to the amino acid sequence of SEQ ID NO:4;
   e) a uricase subunit having an amino acid sequence that is at least 94% identical to the amino acid sequence of SEQ ID NO:5;
   f) a uricase subunit having an amino acid sequence that is at least 93% identical to the amino acid sequence of SEQ ID NO:6;
   g) a uricase subunit having an amino acid sequence that is at least 91% identical to the amino acid sequence of SEQ ID NO:7;
   h) a uricase subunit having an amino acid sequence that is at least 90% identical to the amino acid sequence of SEQ ID NO:8;
   i) a uricase subunit having an amino acid sequence that is at least 98% identical to the amino acid sequence of SEQ ID NO:9; and
   j) any combination of the subunits a. through i. above.

Also provided herein is a vector comprising a nucleic acid molecule encoding one or more uricase subunits of this invention and/or fragments thereof. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, poxvirus, vaccinia virus, adenovirus, retrovirus, alphavirus and/or adeno-associated virus nucleic acid. The nucleic acid molecule or vector of this invention can also be in a liposome or a delivery vehicle, which can be taken up by a cell via receptor-mediated or other type of endocytosis.

The nucleic acid molecule of this invention can be in a cell, which can be a cell expressing the nucleic acid whereby a uricase subunit and/or fragment thereof of this invention is produced in the cell (e.g., a host cell). In addition, the vector of this invention can be in a cell, which can be a cell expressing the nucleic acid of the vector whereby a uricase subunit and/or fragment thereof of this invention is produced in the cell. It is also contemplated that the nucleic acids and/or vectors of this invention can be present in a host organism (e.g., a transgenic organism), which expresses the nucleic acids of this invention and produces the uricase subunits and/or fragments of this invention.

In some embodiments, the nucleic acid molecules encoding the polypeptides and/or fragments of this invention can be part of a recombinant nucleic acid construct comprising any combination of restriction sites and/or functional elements as are well known in the art that facilitate molecular cloning and other recombinant nucleic acid manipulations. Thus, the present invention further provides a recombinant nucleic acid construct comprising a nucleic acid molecule encoding a polypeptide and/or fragment of this invention.

The nucleic acid molecule encoding the polypeptide and/or fragment of this invention can be any nucleic acid molecule that functionally encodes the polypeptides and/or fragments of this invention. To functionally encode the polypeptides and/or fragments (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Non-limiting examples of expression control sequences that can be present in a nucleic acid molecule of this invention include promoters derived from metallothionine genes, actin genes, immunoglobulin genes, CMV, SV40, adenovirus, bovine papilloma virus, etc. A nucleic acid molecule encoding a selected polypeptide and/or fragment can readily be determined based upon the genetic code for the amino acid sequence of the selected polypeptide and/or fragment and many nucleic acids will encode any selected polypeptide and/or fragment. Modifications in the nucleic acid sequence encoding the polypeptide and/or fragment are also contemplated. Modifications that can be useful are modifications to the sequences controlling expression of the polypeptide and/or fragment to make production of the polypeptide and/or fragment inducible or repressible as controlled by the appropriate inducer or repressor. Such methods are standard in the art. The nucleic acid molecule and/or vector of this invention can be generated by means standard in the art, such as by recombinant nucleic acid techniques and/or by synthetic nucleic acid synthesis or in vitro enzymatic synthesis.

The nucleic acids and/or vectors of this invention can be transferred into a host cell (e.g., a prokaryotic or eukaryotic cell) by well known methods, which vary depending on the type of cell host. For example, calcium chloride transfection is commonly used for prokaryotic cells, whereas calcium phosphate treatment, transduction, cationic lipid treatment and/or electroporation can be used for other cell hosts.

Uricase-Producing Cells

Cells that produce one or more uricase subunits and/or uricases of the present invention are also provided. Such cells may comprise one or more nucleic acid molecules and/or vectors of the present invention. Any suitable cell known in the art may be used, including, but not limited to, bacterial cells (e.g., *Escherichia coli* and *Bacillus subtilis*), yeast cells (e.g., *Saccharamyces cerevisiae*), filamentous fungi (e.g., *Aspergillus*), plant cells, animal cells and insect cells.

Cells of the present invention can be maintained in culture under conditions suitable for the expression of one or more uricase subunits of the present invention and/or the formation of one or more uricases of the present invention. Those skilled in the art will appreciate that the conditions suitable for the expression of uricase subunits and/or the formation of uricases may vary depending on the identity of the cells comprising the nucleic acid molecule(s) and/or vector(s) of the present invention, the nucleic acid molecule(s) and/or vector(s) being expressed, the uricase subunit(s) being expressed, etc. Such conditions for culturing cells of this invention are well known in the art.

Uricases of the present invention can be extracted and purified from uricase-producing cells of the present invention using any suitable method known in the art.

Pharmaceutical Compositions/Methods

Uricases, uricase subunits, nucleic acid molecules, vectors and cells of the present invention can be administered to a subject to reduce the amount of uric acid in the subject and/or prevent an increase in the amount of uric acid in the subject. Uricases, uricase subunits, nucleic acid molecules, vectors and cells of the present invention can be used for medical, veterinary and/or research purposes (e.g., they can be tested in uricase-deficient animals, such as $Uox^{+/-}$ or $Uox^{-/-}$ mice (See, e.g., Kelly et al., *J. Am. Soc. Nephrol.* 12:1001-1009 (2001)).

Uricases, nucleic acid molecules, vectors and cells of the present invention (and compositions comprising one or more uricases of the present invention, one or more nucleic acid molecules of the present invention, one or more vectors of the present invention and/or one or more cells of the present invention) can be used therapeutically to treat and/or prevent various disorders, including, but not limited to, hyperuricemia, gout, tumor lysis syndrome and hypertension. In some embodiments, uricases, nucleic acid molecules, vectors and cells of the present invention (and compositions comprising one or more uricases of the present invention, one or more nucleic acid molecules of the present invention, one or more vectors of the present invention and/or one or more cells of the present invention) may be used as a prophylaxis against hyperuricemia caused by tumor lysis syndrome in the treatment of cancer. For example, administration of uricases, nucleic acid molecules, vectors and cells of the present invention (and compositions comprising one or more uricases of the present invention, one or more nucleic acid molecules of the present invention, one or more vectors of the present invention and/or one or more cells of the present invention) to a subject in need thereof (e.g., a subject with cancer and/or a subject undergoing treatment for cancer) can reduce the risk of developing hyperuricemia as well as prevent or delay the onset of hyperuricemia.

Uricases, nucleic acid molecules, vectors and cells of the present invention (and compositions comprising one or more uricases of the present invention, one or more nucleic acid molecules of the present invention, one or more vectors of the present invention and/or one or more cells of the present invention) can be used alone or in combination with other therapeutic agents/compositions, including, but not limited to, allopurinol, known uricases (e.g., Krystexxa™ (Savient Pharmaceuticals, Inc., East Brunswick, N.J.) and/or Elitek® (Sanofi Aventia US, LLC, Bridgewater, N.J.)), uricosuric agents (e.g., probeecid, benzbromarone and/or sulfinpyrazone), and anti-inflammatory agents (e.g., nonsteroidal anti-inflammatory drugs and/or glucocorticoids).

In some embodiments, compositions comprising one or more (unconjugated or conjugated) uricases of the present invention, one or more nucleic acid molecules of the present invention, one or more vectors of the present invention and/or one or more cells of the present invention are provided. Such compositions may comprise additional medicinal agents, stabilizing agents, buffers, carriers, adjuvants, diluents, etc.

Compositions of the present invention may comprise any suitable pharmaceutically acceptable carrier, including, but not limited to, phosphate buffered saline and isotonic saline solution. Other examples of pharmaceutically acceptable carriers may be found, for example, in PHARMACEUTICAL SCIENCES (18th Ed., Mack Publishing Co. (1990)) or REMINGTON: THE SCIENCE AND PRACTICE OF PHARMACY (20th Ed., Lippincott Williams & Wilkins (2000)).

Compositions of the present invention may comprise any suitable diluents(s) or excipient(s), including, but not limited to, those set forth in REMINGTON: THE SCIENCE AND PRACTICE OF PHARMACY (20th Ed., Lippincott Williams & Wilkins (2000)) and HANDBOOK OF PHARMACEUTICAL EXCIPIENTS (6th Ed., American Pharmaceutical Association (2009)).

Compositions of the present invention may be formulated so as to be suitable for administration via any known method, including, but not limited to, oral administration, parenteral administration (including, but not limited to, subcutaneous, intravenous, intramuscular, intrathecal and interperitoneal injection) and topical administration (including, but not limited to, transdermal administration, intranasal administration, vaginal administration, rectal administration and inhalational administration). In some embodiments, the composition is formulated for intravenous injection.

For oral administration, compositions of the present invention may be formulated into solid or liquid preparations (e.g., capsules, pills, tablets, troches, lozenges, melts, powders, solutions, suspensions or emulsions) according to methods known in the art for the manufacture of pharmaceutical compositions.

For parenteral administration, compositions of the present invention may be formulated for subcutaneous, intravenous, intramuscular, intrathecal or interperitoneal injection according to methods known in the art for the manufacture of pharmaceutical compositions. For example, uricases of the present invention may be formulated into injectable dosages with a pharmaceutically acceptable carrier, such as sterile saline or peanut oil. Injectable compositions of the present invention may typically contain about 0.5% to about 25% by weight of the uricase(s) of the present invention. A non-ionic surfactant may be included in a range of about 5% to about 15% by weight to minimize or eliminate irritation at the site of injection. Preservatives and buffers may also be included.

For topical administration, compositions of the present invention may be formulated into a topical cream/lotion/gel or a transdermal patch according to methods known in the art for the manufacture of pharmaceutical compositions. Transdermal patches may be formulated to provide continuous, discontinuous and/or on-demand infusion of uricases of the present invention in controlled amounts.

Methods of reducing the amount of uric acid and/or preventing an increase in the amount of uric acid in a subject can comprise, consist essentially of or consist of administering to the subject an effective amount of one or more (unconjugated or conjugated) uricases of the present invention, one or more nucleic acid molecules of the present invention, one or more vectors of the present invention and/or one or more cells of the present invention.

Methods of treating and/or preventing hyperuricemia, gout, tumor lysis syndrome and/or hypertension can comprise, consist essentially of or consist of administering to the subject an effective amount of one or more (unconjugated or conjugated) uricases of the present invention, one or more nucleic acid molecules of the present invention, one or more vectors of the present invention and/or one or more cells of the present invention.

In some embodiments, the uricase(s), nucleic acid molecule(s), vector(s) and/or cell(s) are administered as part of a composition comprising the uricase(s), nucleic acid molecule(s), vector(s) and/or cell(s) and a pharmaceutically acceptable carrier. As described above, such compositions may comprise any suitable pharmaceutically acceptable carrier, stabilizing agent, buffer, diluents, excipient, adjuvant, etc.

Uricases, nucleic acid molecules, vectors and cells of the present invention can be administered by any method known in the art, including, but not limited to, oral administration, parenteral administration (including, but not limited to, subcutaneous, intravenous, intramuscular, intrathecal injection and interperitoneal injection) and topical administration (including, but not limited to, transdermal administration, intranasal administration, vaginal administration, rectal administration and inhalational administration). In some embodiments, the uricase(s), nucleic acid molecule(s), vector(s) and/or cell(s) are administered via intravenous injection. Uricases, nucleic acid molecules, vectors and cells of the present invention can be administered using any conventional dosage unit/form, One of skill in the art will appreciate that the effective amount of any specific compound will vary somewhat from compound to compound, and patient to patient, and will depend upon the condition of the patient and the route of delivery. The appropriate dosage for a given subject can be determined by methods known in the art. See, e.g., ANSEL'S PHARMACEUTICAL DOSAGE FORMS AND DRUG DELIVERY SYSTEMS (9th Ed., Lippincott Williams and Wilkins (2010)); REMINGTON'S PHARMACEUTICAL SCIENCES (18th Ed., Maack Publishing Company, Easton, Pa. (1990)); REMINGTON: THE SCIENCE AND PRACTICE OF PHARMAC (21st Ed., Lippincott Williams and Wilkins (2005)). In some embodiments, a dosage in a range from about 0.1 mg/kg to about 100 mg/kg will have the desired effect (e.g., therapeutic efficacy), with all weights being calculated based upon the weight of the compound, including the cases where a salt is employed. More than one administration (e.g., two, three, four, five or more administrations) can be employed at a variety of time intervals (e.g., hourly, daily, weekly, monthly, etc.) to achieve the desired effect(s).

In some embodiments, a uricase of the present invention can be administered to a subject in a dosage range of about 0.1 mg to about 20.0 mg of uricase every 1-8 weeks (regardless of body mass or age). For example, about 5 mg to about 10 mg of uricase may be administered to a subject every 2-4 weeks. In an exemplary embodiment, about 8 mg of uricase is administered to a subject every 2 weeks.

In some embodiments, a uricase of the present invention can be administered to a subject in a dosage range of about 0.1 mg per kilogram to about 20.0 mg per kilogram of body weight multiple times over the course of several days (e.g., 3-10 days). For example, about 0.1 to about 1.0 mg of uricase per kilogram of body weight may be administered to a subject once a day for 3-10 days. In particular embodiments, about 0.2 mg of uricase per kilogram of body weight is administered to a subject once a day for 5 days.

The nucleic acid molecules and vectors of this invention can be administered orally, intranasally, parenterally (e.g., intravenously), by intramuscular injection, by intraperitoneal injection, transdermally, transmucosally, extracorporeally, topically or the like. In the methods described herein which include the administration and uptake of exogenous nucleic acid into the cells of a subject (i.e., gene transduction or transfection), the nucleic acid molecules of the present invention can be in the form of naked nucleic acid or the nucleic acid molecules can be in a vector for delivering the nucleic acid molecules to the cells for expression of the polypeptides and/or fragments of this invention. In some embodiments, the vector can be a commercially available preparation or can be constructed in the laboratory according to methods well known in the art. In further embodiments, the vector can be a viral vector, as is well known in the art.

Delivery of the nucleic acid molecule and/or vector of this invention to cells can be via a variety of mechanisms that are well known in the art. As one example, delivery can be via a liposome, using commercially available liposome preparations such as LIPOFECTIN®, LIPOFECTAMINE™

(GIBCO-BRL, Inc., Gaithersburg, Md.), SUPERFECT® (Qiagen, Inc. Hilden, Germany) and TRANSFECTAM® (PromegaBiotec, Inc., Madison, Wis.), as well as other liposomes developed according to procedures standard in the art. In addition, the nucleic acid molecule and/or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

In particular embodiments as described herein, vector delivery can be via a viral system, such as a retroviral vector system, which can package a recombinant retroviral genome. The recombinant retrovirus can then be used to infect and thereby deliver to the infected cells nucleic acid molecules encoding the polypeptide and/or fragment of this invention. The exact method of introducing the exogenous nucleic acid into mammalian cells is, of course, not limited to the use of retroviral vectors. Other techniques are widely available for this procedure including the use of adenoviral vectors, alphaviral vectors, adeno-associated viral (AAV) vectors, lentiviral vectors, pseudo typed retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods.

As one nonlimiting example, the nucleic acid molecule of this invention can be delivered to the cells of a subject in a modified vaccinia virus vector. The dosage for administration of vaccinia-based vectors to humans can typically range from about $10^7$ to about $5 \times 10^9$ plaque forming units (pfu) per injection.

As another nonlimiting example, the nucleic acid molecule of this invention can be delivered to the cells of a subject in an adenovirus vector. The dosage for administration of adenovirus to humans can range from about $10^7$ to about $10^{11}$ pfu per injection.

In some embodiments, a subject will receive a single injection of a viral vector comprising a nucleic acid molecule of this invention. If additional injections are necessary, they can be repeated at daily/weekly/monthly intervals for an indefinite period and/or until the efficacy of the treatment has been established. As set forth herein, the efficacy of treatment can be determined by evaluating the symptoms and clinical parameters described herein.

The exact amount of the nucleic acid molecule and/or vector required will vary from subject to subject, depending on the species, age, weight and general condition of the subject, the particular nucleic acid molecule and/or vector used, its mode of administration and the like. Thus, it is not possible to specify an exact amount for every nucleic acid or vector. However, an appropriate amount can be determined by one of ordinary skill in the art using only routine experimentation given the teachings herein.

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

The following non-limiting examples are provided to further illustrate the present invention.

Example 1

Recombinant Human Uricase

Although the human ukase gene contains two stop codons (and an aberrant slice-acceptor site), these mutations could easily be replaced with sense codons (e.g., the stop codons could be replaced with amino acids derived from homologous uricase sequences) and the resulting open reading frame, minus introns, could serve as a gene for heterologous expression and purification. The purified human uricase protein could then be used for infusion or injection into human subjects.

The mutational events that resulted in the non-functional uricase within the hominoid lineage are predicted to have occurred on the order of 15-20 million years ago. If this is the case, the human uricase has had millions of years to accumulate amino acid replacements due to the loss of selective constraints acting on the gene and these replacements may have diminished and/or abolished catalytic activity.

In the present invention, a molecular evolutionary analysis has been applied in an attempt to better understand the amino acid replacements that have occurred in hominoid uricases as well as the selective constraints governing the evolution of these hominoid uricase genes. These analyses consisted of G-tests to compare the number of synonymous versus non-synonymous substitutions during primate uricase evolution, the dN/dS metric to detect positive selection/adaptive evolution, and mapping amino acid replacements inferred to have occurred during early primate evolution using homology modeling on a three-dimensional uricase structure. These analyses provide strong evidence that primate uricases experienced positive selection early in primate evolution based on the large number of nonsynonymous mutations that replaced amino acids versus a small portion of synonymous mutations during the same time period. The results suggest that primate uricases accumulated amino acids in a manner that actually decreased their enzymatic activity and that there was a selective advantage for this decreased activity. Such results contradict the hypothesis that hominoid uricase has been a pseudogene for 15-20 Ma. Mapping the amino acid replacements that occurred during this time period onto a homologous structure confirmed this. The majority of the amino acid replacements occurred in the active site of the protein (data not shown). This would indicate that ancestral ape primate uricases did not encode highly active uricase even before the stop codons were introduced into these orthologous genes.

To confirm that the human uricase gene would not encode a highly functional uricase even with the removal of the two stop internal stop codons, a recombinant human uricase subunit (SEQ ID NO:9) was engineered wherein the two stop codons were replaced with arginines and the introns were removed from the gene. The recombinant human uricase was cloned into the pET-15b vector (Novagen®, EMD Chemicals, Inc., Gibbstown, N.J.) and expressed in Tuner™ (DE3) cells (Novagen®, EMD Chemicals, Inc., Gibbstown, N.J.). Expression was confirmed via Western blot. Unfortunately, the recombinant human uricase resided in the insoluble fraction during purification. Attempts were made to refold the recombinant human uricase following solubilization with urea or guanidine hydrochloride, but it was not clear whether those attempts were successful because no uricolytic activity was detected following the re-folding attempts. It was not clear whether the lack of uricolytic activity in the samples was the result of a failure to refold the recombinant human uricase properly or an inherent lack of uricolytic activity despite proper refolding.

Next, the recombinant human uricase subunit and a pig uricase subunit (SEQ ID NO:10) were each cloned into a separate pIRESpuro3 mammalian expression vector (ClonTech, Clontech Laboratories, Inc., Mountain View, Calif.) with 5'-EcoRI and 3'-NotI restriction sites and expressed in human hepatocytes. Expression of each uricase was confirmed with an antibody that recognizes an evolutionarily conserved uricase epitope. Uricolytic activity was assessed by comparing the effects of the recombinant human uricase and pig uricase on several markers of uricase activity (intracellular uric acid levels, triglyceride levels and fatty acid synthase levels) in vivo. Unlike pig uricase, the recombinant human uricase possessed no uricolytic activity (data not shown).

Example 2

Resurrecting Ancient Uricases

Uricases were designed using Ancestral Sequence Reconstruction (ASR) to reconstruct and resurrect ancestral forms of human uricase based upon an analysis of modern mammalian uricases. See generally Gaucher, "Ancestral sequence reconstruction as a tool to understand natural history and guide synthetic biology: Realizing (and extending) the vision of Zukerkandl and Pauling" in ANCESTRAL SEQUENCE RECONSTRUCTION, ed. David A. Liberles, pp. 20-33 (Oxford University Press, 2007). Ancestral uricase sequences corresponding to various nodes of the phylogenetic tree were inferred by analyzing modern mammalian uricase sequences (FIG. 1), and uricases were designed based upon those inferred sequences. Uricase subunits of the present invention may therefore comprise an amino acid sequence corresponding to the inferred amino acid sequence at one of the nodes highlighted in FIG. 1 (e.g., Node 18, Node 19, Node 26, Node 27, Node 30, Node 31 or Node 32) or to a variant of the inferred amino acid sequence at one of the nodes highlighted in FIG. 1.

Example 3

Synthetic Uricase Expression

Nucleic acid sequences encoding various uricase subunits of the present invention were each cloned into a pET-21a vector (Novagen®, EMD Chemicals, Inc., Gibbstown, N.J.) using the amino terminal NdeI and the carboxy-terminal XhoI restriction sites. Tuner™ (DE3) cells (Novagen®, EMD Chemicals, Inc., Gibbstown, N.J.) were transformed, and a single colony was used to inoculate 5 ml of Luria Broth (LB), which was incubated overnight at 37° C. Fresh LB (250 mL) containing 100 µg/ml carbenicillin and 100 µg/ml chloramphenicol was seeded with 2.5 ml of overnight culture. Cells were grown to an $OD_{600}$ between 0.6 and 0.8, and expression was induced using a final concentration of 1 mM IPTG. Expression was carried out overnight (16-20 hours) at 37° C. with shaking at 250 rpm. Cells were collected by centrifugation at 5,000×g for 30 minutes at 6° C. and stored at −80° C. in 50 ml conical tubes.

Example 4

Inclusion Body Preparation and Uricase Extraction

Figure 2:
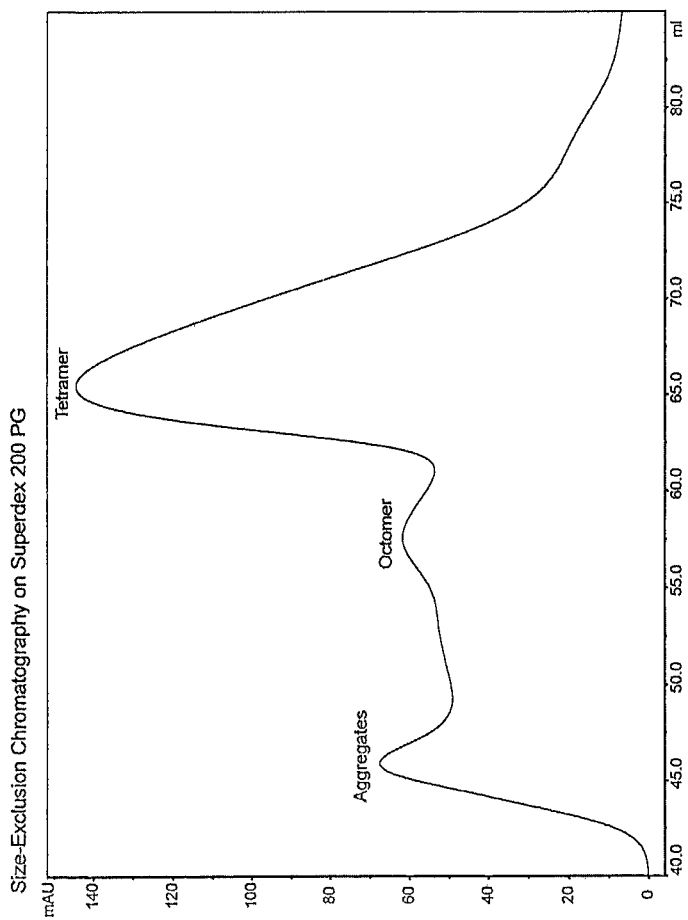
FIG. 2 is a graphical representation of the results of the SDS-PAGE analysis described in Example 3. Lane A contains a Precision Plus Protein™ Kaleidoscope™ Marker (Bio-Rad Laboratories, Inc., Hercules, Calif.). Lane B contains a homotetrameric uricase having uricase subunits with the amino acid sequence of SEQ ID NO:3. Lane C contains a homotetrameric uricase having uricase subunits with the amino acid sequence of SEQ ID NO:4.

Frozen cells from Example 3 were thawed at room temperature and resuspended in 4 ml Bugbuster® Protein Extraction Reagent (Novagen®, EMD Chemicals, Inc., Gibbstown, N.J.) containing 4 µl Benzonase® endonuclease (Novagen®, EMD Chemicals, Inc., Gibbstown, N.J.). Cells were incubated with gentle rocking for 30 min at room temperature. Insoluble uricase was pelleted by centrifugation at 16,000×g for 20 min at 4° C., and the supernatant was discarded. Inclusion bodies were washed overnight in 4 ml of 1M $Na_2CO_3$, pH 10.2 to remove contaminating proteins. Uricase was extracted from the washed inclusion bodies via a 4 hour incubation in 4 ml of 0.5M $Na_2CO_3$, pH 11. Carbonate-insoluble debris was removed by centrifugation at 20,190×g for 30 min at 6° C. The purity of the uricases extracted from the cells was confirmed by the presence of a single 35 kDa band in supernatant samples separated and visualized using SDS-PAGE analysis (See, e.g., FIG. 2). The uricolytic activity of the extracted uricases was confirmed using an Amplex® Red Uricase Assay Kit (Molecular Probes, Inc., Eugene, Oreg.).

Example 5

Purification of Synthetic Uricases

Figure 3:
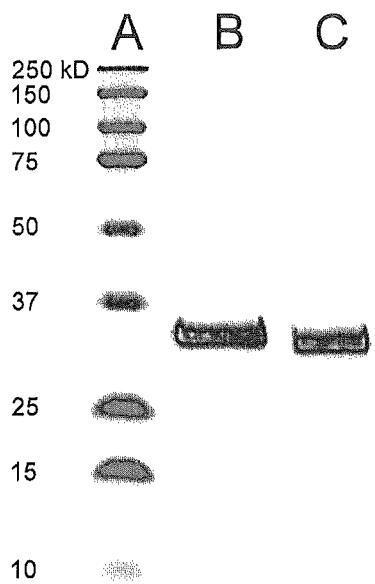
FIG. 3 is a chromatogram depicting the separation of uricase tetramers, octamers and aggregates described in Example 4.

Tetrameric uricases were separated from octameric uricases and larger aggregates in the carbonate extraction supernatant at 4° C. using an ÄKTA™ Design UPC 10 size exclusion chromatography system (GE Healthcare Life Sciences, Piscataway, N.J.). The carbonate extraction supernatants from Example 2 were centrifuged for 20 min at 20,000×g to remove any remaining cell debris, then applied directly to a HiLoad™ 16/60 Superdex™ 200 prep grade column (GE Healthcare Life Sciences, Piscataway, N.J.) pre-equilibrated with 0.1M $Na_2CO_3$, pH 11. Tetrameric uricase was eluted at around 65 ml (as monitored by absorbance at 280 nm; FIG. 3). This peak was collected in 2 ml fractions, pooled and concentrated by centrifugation using Pierce Protein Concentrators (Thermo Fisher Scientific, Inc., Rockford, Ill.).

Example 6

Uricolytic Activity of Synthetic Uricases

The uricolytic activities of the uricases collected in Example 5 and previously known uricases were determined spectrophotometrically by monitoring decreases in absorbance at the absorption maxima of uric acid (293 nm; hereinafter "$A_{293}$"). Reactions were performed in 1 ml reaction volumes in quartz cuvettes at 24° C. or 37° C. using the following uric acid concentrations: 1 µM, 2.5 µM, 5 µM, 10 µM, 15 µM, 20 µM, 25 µM, 50 µM, 75 µM and 100 µM. The amount of uricase added to each reaction was adjusted to give a linear decrease in uric acid over the 6 minute time course of the assay. The initial velocity of each reaction was determined by plotting the decrease in $A_{293}$ versus time and determining the slope in the linear portion of the curve. Each assay was run in triplicate, and the average initial velocity of each assay was used to plot a hyperbolic regression curve to determine the Michaelis Constant ($K_M$) and the maximum reaction rate ($V_{max}$) of the corresponding uricase. The concentration of uricase in each assay was determined using a Quick Start™

Bradford Assay (Bio-Rad Laboratories, Inc., Hercules, Calif.) and used to determine $k_{cat}$ for each uricase.

The kinetic parameters of several uricases are described in Table 3, including pig uricase (each subunit having the amino acid sequence of SEQ ID NO:10), a pig-baboon chimeric uricase (the first 225 amino acids of each subunit corresponding to amino acids 1-225 of SEQ ID NO:10 and the remaining 79 amino acids of each subunit corresponding to amino acids 226-304 of SEQ ID NO:11)), a uricase comprising four identical uricase subunits having the amino acid sequence of SEQ ID NO:2 ("Node 19"), a uricase comprising four identical uricase subunits having the amino acid sequence of SEQ ID NO:3 ("Node 26") and a uricase comprising four identical uricase subunits having the amino acid sequence of SEQ ID NO:4 ("Node 27").

TABLE 3

| | $V_{max}$ (μmol uric acid/min) | $K_M$ (μM uric acid) | $k_{cat}$ (min$^{-1}$) |
|---|---|---|---|
| Pig Uricase * α | $2.4 \times 10^{-3}$ | 2.1 | 470 |
| Pig-Baboon Uricase * α | $2.8 \times 10^{-3}$ | 2.2 | 287 |
| Node 19 * α | $4.3 \times 10^{-3}$ | 4.0 | 325 |
| Node 26 ** α | $1.4 \times 10^{-3}$ | 4.9 | 75 |
| Node 27 ** α | $8.1 \times 10^{-4}$ | 5.3 | 25 |
| Node 26 ** β | $4.3 \times 10^{-3}$ | 4.9 | 225 |

\* in 0.1M Na$_2$HPO$_4$/Na$_2$H$_2$PO$_4$, pH 7.4
\*\* in phosphate buffered saline, pH 7.4
α tested at 24° C.
β tested at 37° C.

Example 7

In vivo Testing

Uricases, uricase subunits, nucleic acid molecules, vectors and cells of the present invention can be tested using various in vivo testing protocols. For example, uricases, uricase subunits, nucleic acid molecules, vectors and cells of the present invention can be tested in uricase-deficient animals, such as Uox$^{+/-}$ or Uox$^{-/-}$ mice (See, e.g., Kelly et al., J. Am. Soc. Nephrol. 12:1001-1009 (2001)).

Example 8

Reducing Uric Acid Levels in a Human Subject

As one nonlimiting example of this invention, a human subject whose initial uric acid level is at least 6.0 mg/dL in blood plasma can be administered a dose of about 5 mg to about 10 mg (e.g., about 8 mg) of a uricase of the present invention (e.g., a uricase comprising four identical uricase subunits comprising the amino acid sequence of SEQ ID NO:2) via intravenous injection every two weeks for twelve weeks. The subject's uric acid level can be monitored over the twelve week treatment period, with the treatment goal of maintaining the subject's uric acid level at a mean of about 1.0 mg/dL.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A uricase comprising at least one uricase subunit comprising the amino acid sequence of SEQ ID NO:8, wherein $X_1$ is N; $X_2$ is D; $X_3$ is Y; $X_4$ is K; $X_5$ is D; $X_6$ is D; $X_7$ is M; $X_8$ is Y; $X_9$ is S; $X_{10}$ is S; $X_{11}$ is G; $X_{12}$ is S; $X_{13}$ is A; $X_{14}$ is M; $X_{15}$ is C; $X_{16}$ is E; $X_{17}$ is N; $X_{18}$ is V; $X_{19}$ is V; $X_{20}$ is R; $X_{21}$ is F; $X_{22}$ is E: $X_{23}$ is K; $X_{24}$ is M; $X_{25}$ is R; $X_{26}$ is S; $X_{27}$ is P; $X_{28}$ is K; $X_{29}$ is Q; $X_{30}$ to is F; $X_{31}$ is Q; $X_{32}$ is H; $X_{33}$ is G; $X_{34}$ is D; $X_{35}$ is E; $X_{36}$ is T; $X_{37}$ is V; $X_{38}$ is R; $X_{40}$ is L; $X_{41}$ is L; $X_{41}$ is E; $X_{42}$ is F; $X_{43}$ is G; $X_{44}$ is E; $X_{45}$ is S; $X_{46}$ is P; $X_{47}$ is Y; $X_{48}$ is E; $X_{49}$ is Y; $X_{50}$ is M; $X_{51}$ is D; and $X_{52}$ is R and said uricase has enhanced uricolytic activity relative to a control uricase.

2. The uricase of claim 1, wherein the uricase is a homotetramer or a homooctamer.

3. The uricase of claim 1, wherein the uricase is conjugated to one or more oligomers.

4. A composition comprising the uricase of claim 1, in a pharmaceutically acceptable carrier.

* * * * *

UNITED STATES PATENT AND TRADEMARK OFFICE
CERTIFICATE OF CORRECTION

PATENT NO.         : 8,940,861 B2                                    Page 1 of 1
APPLICATION NO.    : 13/083011
DATED              : January 27, 2015
INVENTOR(S)        : Gaucher It is certified that error appears in the above-identified patent and that said Letters Patent is hereby corrected as shown below:

In the Specification:
Column 17, Line 40: Please correct "unease" to read -- uricase --
Column 17, Line 49: Please correct "unease" to read -- uricase --
Column 17, Line 50: Please correct "unease" to read -- uricase --
Column 17, Line 51: Please correct "unease" to read -- uricase --
Column 17, Line 52: Please correct "unease" to read -- uricase --
Column 17, Line 53: Please correct "unease" to read -- uricase --
Column 17, Line 55: Please correct "unease" to read -- uricase --
Column 17, Line 56: Please correct "unease" to read -- uricase --
Column 17, Line 57: Please correct "unease" to read -- uricase --
Column 17, Line 60: Please correct "unease." to read -- uricase. --

Column 24, Line 10: Please correct "ukase" to read -- uricase --

In the Claims:
Column 51, Claim 1, Lines 46 and 47:
    Please correct "$X_{38}$ is R; $X_{40}$ is L; $X_{41}$ is L; $X_{41}$ is E; $X_{42}$ is F;"
    to read -- $X_{38}$ is R; $X_{39}$ is I; $X_{40}$ is L; $X_{41}$ is E; $X_{42}$ is F; --

Signed and Sealed this
Twenty-ninth Day of September, 2015

Michelle K. Lee
*Director of the United States Patent and Trademark Office*

```
                     SEQUENCE LISTING

<160> NUMBER OF SEQ ID NOS: 11

<210> SEQ ID NO 1
<211> LENGTH: 304
<212> TYPE: PRT
<213> ORGANISM: Artificial
<220> FEATURE:
<223> OTHER INFORMATION: Synthetic uricase sequence

<400> SEQUENCE: 1

Met Ala His Tyr His Gly His Leu Thr Lys Asn Ala Glu Val Glu Phe
1               5                   10                  15

Val Arg Thr Gly Tyr Gly Lys Asp Val Val Lys Val Leu His Ile Gln
            20                  25                  30

Arg Asp Gly Lys His His Ile Ile Lys Glu Val Ala Thr Ser Val Gln
        35                  40                  45

Leu Thr Leu Asn Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Thr Ile Glu Ala Phe Ala Met Asn Ile Gly Lys
                85                  90                  95

His Phe Leu Ser Ser Phe Asn His Val Ile Arg Ala Gln Val Tyr Val
            100                 105                 110
```

```
Glu Glu Val Pro Trp Lys Arg Phe Glu Lys Asn Gly Val Asn His Val
            115                 120                 125

His Ala Phe Ile His Thr Pro Thr Gly Thr His Phe Cys Glu Val Glu
        130                 135                 140

Gln Lys Arg Gly Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Arg Phe Thr Thr Leu Pro Glu Val Lys Asp Arg Cys Phe Ala Thr Gln
            180                 185                 190

Val Tyr Cys Lys Trp Arg Tyr Asp Gln Ser Arg Ala Val Asp Phe Glu
        195                 200                 205

Ala Ile Trp Asp Thr Val Leu Asp Ile Val Leu Glu Lys Phe Ala Gly
        210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
        290                 295                 300

<210> SEQ ID NO 2
<211> LENGTH: 304
<212> TYPE: PRT
<213> ORGANISM: Artificial
<220> FEATURE:
<223> OTHER INFORMATION: Synthetic uricase sequence

<400> SEQUENCE: 2

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
        50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Ala Met Asn Ile Cys Glu
                85                  90                  95

His Phe Leu Ser Ser Phe Asn His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile His Thr Pro Thr Gly Thr His Phe Cys Glu Val Glu
    130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175
```

```
Gln Phe Thr Thr Leu Pro Glu Val Lys Asp Arg Cys Phe Ala Thr Gln
                180                 185                 190

Val Tyr Cys Lys Trp Arg Tyr His Gln Gly Arg Asp Val Asp Phe Glu
            195                 200                 205

Ala Thr Trp Asp Thr Val Arg Asp Ile Val Leu Glu Lys Phe Ala Gly
        210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
290                 295                 300
```

<210> SEQ ID NO 3
<211> LENGTH: 304
<212> TYPE: PRT
<213> ORGANISM: Artificial
<220> FEATURE:
<223> OTHER INFORMATION: Synthetic uricase sequence

<400> SEQUENCE: 3

```
Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Ala Val Asn Ile Cys Glu
                85                  90                  95

His Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Asp Thr Ile Arg Asp Leu Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240
```

```
Asp Ile Gln Val Leu Ser Leu Ser Arg Val Pro Glu Ile Glu Asp Met
            245                 250                 255

Glu Ile Ser Leu Pro Asn Ile His Tyr Phe Asn Ile Asp Met Ser Lys
        260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
        290                 295                 300

<210> SEQ ID NO 4
<211> LENGTH: 304
<212> TYPE: PRT
<213> ORGANISM: Artificial
<220> FEATURE:
<223> OTHER INFORMATION: Synthetic uricase sequence

<400> SEQUENCE: 4

Met Ala His Tyr His Asn Asn Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu
                85                  90                  95

His Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Asp Thr Ile Arg Asp Leu Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
        290                 295                 300
```

<210> SEQ ID NO 5
<211> LENGTH: 304
<212> TYPE: PRT
<213> ORGANISM: Artificial
<220> FEATURE:
<223> OTHER INFORMATION: Synthetic uricase sequence

<400> SEQUENCE: 5

```
Met Ala His Tyr His Asn Asn Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu
                85                  90                  95

His Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Asp Thr Ile Arg Asp Leu Val Leu Glu Lys Ser Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```

<210> SEQ ID NO 6
<211> LENGTH: 304
<212> TYPE: PRT
<213> ORGANISM: Artificial
<220> FEATURE:
<223> OTHER INFORMATION: Synthetic uricase sequence

<400> SEQUENCE: 6

```
Met Ala His Tyr His Asn Asn Tyr Lys Lys Asn Asp Glu Val Glu Phe
1               5                   10                  15
```

```
Val Arg Thr Gly Tyr Gly Lys Asp Met Val Lys Val Leu His Ile Gln
         20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
     50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu
                 85                  90                  95

His Phe Leu Ser Ser Phe Asn His Val Ile Arg Ala Gln Val Tyr Val
                100                 105                 110

Glu Glu Ile Pro Trp Lys His Leu Glu Lys Asn Gly Val Lys His Val
            115                 120                 125

His Ala Phe Ile His Thr Pro Thr Gly Thr His Phe Cys Glu Val Glu
        130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
                180                 185                 190

Val Tyr Cys Lys Trp Arg Tyr His Gln Cys Arg Asp Val Asp Phe Glu
            195                 200                 205

Ala Thr Trp Asp Thr Ile Arg Asp Leu Val Leu Glu Lys Ser Ala Gly
        210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
                260                 265                 270

Met Gly Leu Ile Asn Lys Glu Glu Val Leu Leu Pro Leu Asp Asn Pro
            275                 280                 285

Tyr Gly Lys Ile Thr Gly Thr Val Lys Arg Lys Leu Ser Ser Arg Leu
290                 295                 300

<210> SEQ ID NO 7
<211> LENGTH: 304
<212> TYPE: PRT
<213> ORGANISM: Artificial
<220> FEATURE:
<223> OTHER INFORMATION: Synthetic uricase sequence

<400> SEQUENCE: 7

Met Ala His Tyr His Asn Asn Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80
```

```
Phe Lys Glu Ile Lys Ser Ile Glu Ala Phe Gly Val Asn Ile Cys Glu
                85                  90                  95

His Phe Leu Ser Ser Phe Asn His Val Ile Arg Ala Gln Val Tyr Val
            100                 105                 110

Glu Glu Ile Pro Trp Lys His Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Gln Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Lys
        195                 200                 205

Ala Thr Trp Asp Thr Ile Arg Asp Leu Val Met Glu Lys Ser Ala Gly
    210                 215                 220

Pro Tyr Asp Lys Asp Glu Tyr Ser Pro Ser Val Gln Lys Thr Leu Cys
225                 230                 235                 240

Asp Ile Gln Val Leu Ser Leu Ser Arg Val Pro Ala Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300

<210> SEQ ID NO 8
<211> LENGTH: 304
<212> TYPE: PRT
<213> ORGANISM: Artificial
<220> FEATURE:
<223> OTHER INFORMATION: Synthetic uricase sequence
<220> FEATURE:
<221> NAME/KEY: MISC_FEATURE
<222> LOCATION: (6)..(6)
<223> OTHER INFORMATION: Xaa is Asn or Gly
<220> FEATURE:
<221> NAME/KEY: MISC_FEATURE
<222> LOCATION: (7)..(7)
<223> OTHER INFORMATION: Xaa is Asp, Asn or His
<220> FEATURE:
<221> NAME/KEY: MISC_FEATURE
<222> LOCATION: (8)..(8)
<223> OTHER INFORMATION: Xaa is Tyr or Leu
<220> FEATURE:
<221> NAME/KEY: MISC_FEATURE
<222> LOCATION: (9)..(9)
<223> OTHER INFORMATION: Xaa is Lys or Thr
<220> FEATURE:
<221> NAME/KEY: MISC_FEATURE
<222> LOCATION: (12)..(12)
<223> OTHER INFORMATION: Xaa is Asp or Ala
<220> FEATURE:
<221> NAME/KEY: MISC_FEATURE
<222> LOCATION: (24)..(24)
<223> OTHER INFORMATION: Xaa is Asp or Glu
<220> FEATURE:
<221> NAME/KEY: MISC_FEATURE
<222> LOCATION: (25)..(25)
<223> OTHER INFORMATION: Xaa is Met or Val
<220> FEATURE:
```

```
<221> NAME/KEY: MISC_FEATURE
<222> LOCATION: (37)..(37)
<223> OTHER INFORMATION: Xaa is Tyr or His
<220> FEATURE:
<221> NAME/KEY: MISC_FEATURE
<222> LOCATION: (39)..(39)
<223> OTHER INFORMATION: Xaa is Ser or Ile
<220> FEATURE:
<221> NAME/KEY: MISC_FEATURE
<222> LOCATION: (52)..(52)
<223> OTHER INFORMATION: Xaa is Ser or Asn
<220> FEATURE:
<221> NAME/KEY: MISC_FEATURE
<222> LOCATION: (83)..(83)
<223> OTHER INFORMATION: Xaa is Gly or Glu
<220> FEATURE:
<221> NAME/KEY: MISC_FEATURE
<222> LOCATION: (86)..(86)
<223> OTHER INFORMATION: Xaa is Ser or Thr
<220> FEATURE:
<221> NAME/KEY: MISC_FEATURE
<222> LOCATION: (91)..(91)
<223> OTHER INFORMATION: Xaa is Ala or Gly
<220> FEATURE:
<221> NAME/KEY: MISC_FEATURE
<222> LOCATION: (92)..(92)
<223> OTHER INFORMATION: Xaa is Met or Val
<220> FEATURE:
<221> NAME/KEY: MISC_FEATURE
<222> LOCATION: (95)..(95)
<223> OTHER INFORMATION: Xaa is Cys or Gly
<220> FEATURE:
<221> NAME/KEY: MISC_FEATURE
<222> LOCATION: (96)..(96)
<223> OTHER INFORMATION: Xaa is Glu or Lys
<220> FEATURE:
<221> NAME/KEY: MISC_FEATURE
<222> LOCATION: (103)..(103)
<223> OTHER INFORMATION: Xaa is Asn or Lys
<220> FEATURE:
<221> NAME/KEY: MISC_FEATURE
<222> LOCATION: (112)..(112)
<223> OTHER INFORMATION: Xaa is Val or Met
<220> FEATURE:
<221> NAME/KEY: MISC_FEATURE
<222> LOCATION: (115)..(115)
<223> OTHER INFORMATION: Xaa is Val or Ile
<220> FEATURE:
<221> NAME/KEY: MISC_FEATURE
<222> LOCATION: (119)..(119)
<223> OTHER INFORMATION: Xaa is Arg or His
<220> FEATURE:
<221> NAME/KEY: MISC_FEATURE
<222> LOCATION: (120)..(120)
<223> OTHER INFORMATION: Xaa is Phe or Leu
<220> FEATURE:
<221> NAME/KEY: MISC_FEATURE
<222> LOCATION: (121)..(121)
<223> OTHER INFORMATION: Xaa is Glu or Gly
<220> FEATURE:
<221> NAME/KEY: MISC_FEATURE
<222> LOCATION: (126)..(126)
<223> OTHER INFORMATION: Xaa is Lys or Asn
<220> FEATURE:
<221> NAME/KEY: MISC_FEATURE
<222> LOCATION: (146)..(146)
<223> OTHER INFORMATION: Xaa is Met, Leu or Lys
<220> FEATURE:
<221> NAME/KEY: MISC_FEATURE
<222> LOCATION: (147)..(147)
<223> OTHER INFORMATION: Xaa is Arg or Lys
<220> FEATURE:
<221> NAME/KEY: MISC_FEATURE
<222> LOCATION: (148)..(148)
<223> OTHER INFORMATION: Xaa is Ser or Gly
<220> FEATURE:
<221> NAME/KEY: MISC_FEATURE
<222> LOCATION: (151)..(151)
<223> OTHER INFORMATION: Xaa is Pro or Gln
```

```
<220> FEATURE:
<221> NAME/KEY: MISC_FEATURE
<222> LOCATION: (175)..(175)
<223> OTHER INFORMATION: Xaa is Lys or Arg
<220> FEATURE:
<221> NAME/KEY: MISC_FEATURE
<222> LOCATION: (177)..(177)
<223> OTHER INFORMATION: Xaa is Gln, Arg or Glu
<220> FEATURE:
<221> NAME/KEY: MISC_FEATURE
<222> LOCATION: (178)..(178)
<223> OTHER INFORMATION: Xaa is Phe or Tyr
<220> FEATURE:
<221> NAME/KEY: MISC_FEATURE
<222> LOCATION: (192)..(192)
<223> OTHER INFORMATION: Xaa is Gln or Lys
<220> FEATURE:
<221> NAME/KEY: MISC_FEATURE
<222> LOCATION: (200)..(200)
<223> OTHER INFORMATION: Xaa is His or Asp
<220> FEATURE:
<221> NAME/KEY: MISC_FEATURE
<222> LOCATION: (202)..(202)
<223> OTHER INFORMATION: Xaa is Gly, Cys or Ser
<220> FEATURE:
<221> NAME/KEY: MISC_FEATURE
<222> LOCATION: (204)..(204)
<223> OTHER INFORMATION: Xaa is Asp or Ala
<220> FEATURE:
<221> NAME/KEY: MISC_FEATURE
<222> LOCATION: (208)..(208)
<223> OTHER INFORMATION: Xaa is Glu or Lys
<220> FEATURE:
<221> NAME/KEY: MISC_FEATURE
<222> LOCATION: (210)..(210)
<223> OTHER INFORMATION: Xaa is Thr or Ile
<220> FEATURE:
<221> NAME/KEY: MISC_FEATURE
<222> LOCATION: (214)..(214)
<223> OTHER INFORMATION: Xaa is Val or Ile
<220> FEATURE:
<221> NAME/KEY: MISC_FEATURE
<222> LOCATION: (215)..(215)
<223> OTHER INFORMATION: Xaa is Arg or Leu
<220> FEATURE:
<221> NAME/KEY: MISC_FEATURE
<222> LOCATION: (217)..(217)
<223> OTHER INFORMATION: Xaa is Ile or Leu
<220> FEATURE:
<221> NAME/KEY: MISC_FEATURE
<222> LOCATION: (219)..(219)
<223> OTHER INFORMATION: Xaa is Leu or Met
<220> FEATURE:
<221> NAME/KEY: MISC_FEATURE
<222> LOCATION: (220)..(220)
<223> OTHER INFORMATION: Xaa is Glu or Lys
<220> FEATURE:
<221> NAME/KEY: MISC_FEATURE
<222> LOCATION: (222)..(222)
<223> OTHER INFORMATION: Xaa is Phe or Ser
<220> FEATURE:
<221> NAME/KEY: MISC_FEATURE
<222> LOCATION: (229)..(229)
<223> OTHER INFORMATION: Xaa is Gly or Asp
<220> FEATURE:
<221> NAME/KEY: MISC_FEATURE
<222> LOCATION: (230)..(230)
<223> OTHER INFORMATION: Xaa is Glu or Lys
<220> FEATURE:
<221> NAME/KEY: MISC_FEATURE
<222> LOCATION: (232)..(232)
<223> OTHER INFORMATION: Xaa is Ser or Leu
<220> FEATURE:
<221> NAME/KEY: MISC_FEATURE
<222> LOCATION: (233)..(233)
<223> OTHER INFORMATION: Xaa is Pro or Thr
<220> FEATURE:
<221> NAME/KEY: MISC_FEATURE
<222> LOCATION: (240)..(240)
```

-continued

```
<223> OTHER INFORMATION: Xaa is Tyr or Cys
<220> FEATURE:
<221> NAME/KEY: MISC_FEATURE
<222> LOCATION: (252)..(252)
<223> OTHER INFORMATION: Xaa is Glu or Ala
<220> FEATURE:
<221> NAME/KEY: MISC_FEATURE
<222> LOCATION: (265)..(265)
<223> OTHER INFORMATION: Xaa is Tyr or Leu
<220> FEATURE:
<221> NAME/KEY: MISC_FEATURE
<222> LOCATION: (273)..(273)
<223> OTHER INFORMATION: Xaa is Met or Gly
<220> FEATURE:
<221> NAME/KEY: MISC_FEATURE
<222> LOCATION: (286)..(286)
<223> OTHER INFORMATION: Xaa is Asp, Ser or Cys
<220> FEATURE:
<221> NAME/KEY: MISC_FEATURE
<222> LOCATION: (303)..(303)
<223> OTHER INFORMATION: Xaa is Arg or Lys

<400> SEQUENCE: 8

Met Ala His Tyr His Xaa Xaa Xaa Xaa Lys Asn Xaa Glu Val Glu Phe
1               5                   10                  15

Val Arg Thr Gly Tyr Gly Lys Xaa Xaa Val Lys Val Leu His Ile Gln
            20                  25                  30

Arg Asp Gly Lys Xaa His Xaa Ile Lys Glu Val Ala Thr Ser Val Gln
        35                  40                  45

Leu Thr Leu Xaa Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65              70                  75                  80

Phe Lys Xaa Ile Lys Xaa Ile Glu Ala Phe Xaa Xaa Asn Ile Xaa Xaa
                85                  90                  95

His Phe Leu Ser Ser Phe Xaa His Val Ile Arg Ala Gln Val Tyr Xaa
            100                 105                 110

Glu Glu Xaa Pro Trp Lys Xaa Xaa Xaa Lys Asn Gly Val Xaa His Val
        115                 120                 125

His Ala Phe Ile His Thr Pro Thr Gly Thr His Phe Cys Glu Val Glu
130                 135                 140

Gln Xaa Xaa Xaa Gly Pro Xaa Val Ile His Ser Gly Ile Lys Asp Leu
145                 150                 155                 160

Lys Val Leu Lys Thr Thr Gln Ser Gly Phe Glu Gly Phe Ile Xaa Asp
                165                 170                 175

Xaa Xaa Thr Thr Leu Pro Glu Val Lys Asp Arg Cys Phe Ala Thr Xaa
            180                 185                 190

Val Tyr Cys Lys Trp Arg Tyr Xaa Gln Xaa Arg Xaa Val Asp Phe Xaa
        195                 200                 205

Ala Xaa Trp Asp Thr Xaa Xaa Asp Xaa Val Xaa Xaa Lys Xaa Ala Gly
210                 215                 220

Pro Tyr Asp Lys Xaa Xaa Tyr Xaa Xaa Ser Val Gln Lys Thr Leu Xaa
225                 230                 235                 240

Asp Ile Gln Val Leu Ser Leu Ser Arg Val Pro Xaa Ile Glu Asp Met
                245                 250                 255

Glu Ile Ser Leu Pro Asn Ile His Xaa Phe Asn Ile Asp Met Ser Lys
            260                 265                 270

Xaa Gly Leu Ile Asn Lys Glu Glu Val Leu Leu Pro Leu Xaa Asn Pro
        275                 280                 285

Tyr Gly Lys Ile Thr Gly Thr Val Lys Arg Lys Leu Ser Ser Xaa Leu
```

<210> SEQ ID NO 9
<211> LENGTH: 304
<212> TYPE: PRT
<213> ORGANISM: Artificial
<220> FEATURE:
<223> OTHER INFORMATION: Synthetic uricase sequence

<400> SEQUENCE: 9

```
Met Ala His Tyr His Asn Asn Tyr Lys Lys Asn Asp Glu Val Glu Phe
1               5                   10                  15

Val Arg Thr Gly Tyr Gly Lys Glu Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Glu Ile Lys Ser Ile Glu Ala Phe Gly Val Asn Ile Cys Glu
                85                  90                  95

His Phe Leu Ser Ser Phe Asn His Val Ile Arg Ala Gln Val Tyr Met
            100                 105                 110

Glu Glu Ile Pro Trp Lys His Leu Gly Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Gln Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Lys
        195                 200                 205

Ala Thr Trp Asp Thr Ile Arg Asp Leu Val Met Glu Lys Ser Ala Gly
    210                 215                 220

Pro Tyr Asp Lys Gly Glu Tyr Leu Thr Ser Val Gln Lys Thr Leu Cys
225                 230                 235                 240

Asp Ile Gln Val Leu Ser Leu Ser Arg Val Pro Ala Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```

<210> SEQ ID NO 10
<211> LENGTH: 304
<212> TYPE: PRT
<213> ORGANISM: Sus scrofa

<400> SEQUENCE: 10

```
Met Ala His Tyr Arg Asn Asp Tyr Lys Lys Asn Asp Glu Val Glu Phe
1               5                   10                  15
```

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
        50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Arg Ile Thr Gly Thr Val Lys Arg Lys Leu Thr Ser Arg Leu
290                 295                 300

<210> SEQ ID NO 11
<211> LENGTH: 304
<212> TYPE: PRT
<213> ORGANISM: Papio hamadryas

<400> SEQUENCE: 11

Met Ala Asp Tyr His Asn Asn Tyr Lys Lys Asn Asp Glu Leu Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
        50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu

```
                       85                    90                    95
Tyr Phe Leu Ser Ser Phe Asn His Val Ile Arg Ala Gln Val Tyr Val
            100               105              110

Glu Glu Ile Pro Trp Lys Arg Leu Glu Lys Asn Gly Val Lys His Val
            115               120              125

His Ala Phe Ile His Thr Pro Thr Gly Thr His Phe Cys Glu Val Glu
130             135                      140

Gln Leu Arg Ser Gly Pro Pro Val Ile His Ser Gly Ile Lys Asp Leu
145             150                155              160

Lys Val Leu Lys Thr Thr Gln Ser Gly Phe Glu Gly Phe Ile Lys Asp
                165             170              175

Gln Phe Thr Thr Leu Pro Glu Val Lys Asp Arg Cys Phe Ala Thr Gln
                180             185              190

Val Tyr Cys Lys Trp Arg Tyr His Gln Cys Arg Asp Val Asp Phe Glu
            195             200              205

Ala Thr Trp Gly Thr Ile Arg Asp Leu Val Leu Glu Lys Phe Ala Gly
        210             215             220

Pro Tyr Asp Lys Gly Glu Tyr Ser Pro Ser Val Gln Lys Thr Leu Tyr
225             230             235             240

Asp Ile Gln Val Leu Ser Leu Ser Arg Val Pro Glu Ile Glu Asp Met
                245             250             255

Glu Ile Ser Leu Pro Asn Ile His Tyr Phe Asn Ile Asp Met Ser Lys
            260             265             270

Met Gly Leu Ile Asn Lys Glu Glu Val Leu Leu Pro Leu Asp Asn Pro
        275             280             285

Tyr Gly Lys Ile Thr Gly Thr Val Lys Arg Lys Leu Ser Ser Arg Leu
290             295             300
```